(12) United States Patent
Eisele et al.

(10) Patent No.: US 11,918,819 B2
(45) Date of Patent: Mar. 5, 2024

(54) FACILITATING ACCELERATION OF ADVERTISING RATES FOR MEDICAL DEVICES

(71) Applicant: Medtronic, Inc., Minneapolis, MN (US)

(72) Inventors: Val D. Eisele, New Brighton, MN (US); Robert M. Ecker, Lino Lakes, MN (US); David J. Peichel, Minneapolis, MN (US); William J. Plombon, Forest Lake, MN (US); James D. Reinke, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 644 days.

(21) Appl. No.: 16/670,522

(22) Filed: Oct. 31, 2019

(65) Prior Publication Data

US 2020/0129773 A1 Apr. 30, 2020

Related U.S. Application Data

(60) Provisional application No. 62/753,513, filed on Oct. 31, 2018.

(51) Int. Cl.
*A61N 1/372* (2006.01)
*A61B 5/29* (2021.01)
(Continued)

(52) U.S. Cl.
CPC ............ *A61N 1/37276* (2013.01); *A61B 5/29* (2021.01); *A61N 1/3956* (2013.01); *H04W 4/80* (2018.02)

(58) Field of Classification Search
CPC .............. A61N 1/37252; A61N 1/3956; A61N 1/37276; H04W 4/80
See application file for complete search history.

(56) References Cited

U.S. PATENT DOCUMENTS

| 6,993,393 B2 | 1/2006 | Von Arx et al. |
| 7,127,300 B2 | 10/2006 | Mazar et al. |

(Continued)

OTHER PUBLICATIONS

U.S. Appl. No. 16/263,752, filed Jan. 31, 2019, by Yoon et al.
International Search Report and Written Opinion of International Application No. PCT/US2019/059186, dated Feb. 6, 2020, 14 pp.

*Primary Examiner* — Allen Porter
*Assistant Examiner* — Adreanne A. Arnold
(74) *Attorney, Agent, or Firm* — Shumaker & Sieffert, P.A.

(57) ABSTRACT

Techniques for facilitating communication between an implantable medical device and an external device are provided. In one example, a method comprises broadcasting, via communication circuitry of an implantable device, a first set of advertisements at a first advertising rate according to a communication protocol. The method further comprises determining that detection circuitry of the implantable device detected voltage induced by an electromagnetic field at an interface between tissue of a patient and electrodes of the implantable device and in response to the detection of voltage induced by the electromagnetic field, broadcasting, via the communication circuitry, a second set of advertisements at a second advertising rate according to the communication protocol. The second advertising rate is greater than the first advertising rate.

17 Claims, 18 Drawing Sheets

(51) Int. Cl.
    *A61N 1/39*      (2006.01)
    *H04W 4/80*      (2018.01)

(56)            References Cited

U.S. PATENT DOCUMENTS

| | | | |
|---|---|---|---|
| 8,083,674 | B2 | 12/2011 | Such et al. |
| 8,326,424 | B2 | 12/2012 | Bange et al. |
| 8,538,528 | B2 | 9/2013 | Von Arx et al. |
| 9,288,614 | B1 * | 3/2016 | Young ................ A61N 1/37254 |
| 9,687,658 | B2 | 6/2017 | Wu et al. |
| 9,808,632 | B2 | 11/2017 | Reinke et al. |
| 9,855,433 | B2 | 1/2018 | Shahandeh et al. |
| 2008/0071328 | A1 | 3/2008 | Haubrich et al. |
| 2012/0108922 | A1 | 5/2012 | Schell et al. |
| 2012/0172941 | A1 | 7/2012 | Rys |
| 2012/0192690 | A1 | 7/2012 | Anderson et al. |
| 2013/0244700 | A1 * | 9/2013 | Elias ..................... G01B 7/003 |
| | | | 455/456.6 |
| 2014/0214104 | A1 | 7/2014 | Greenhut et al. |
| 2014/0330327 | A1 | 11/2014 | Thompson-Nauman et al. |
| 2015/0133951 | A1 | 5/2015 | Seifert et al. |
| 2015/0341785 | A1 | 11/2015 | Young et al. |
| 2017/0312530 | A1 * | 11/2017 | Schilling ................ G16H 40/67 |
| 2018/0028827 | A1 | 2/2018 | Schilling et al. |
| 2018/0056080 | A1 * | 3/2018 | Reinke ................ A61N 1/3621 |
| 2018/0243568 | A1 | 8/2018 | Demmer et al. |
| 2018/0295667 | A1 | 10/2018 | Hellman et al. |

* cited by examiner $$Bcoil(z) := \frac{\mu_0}{2} \cdot Icoil \cdot \frac{Rcoil^2}{(Rcoil^2 + z^2)^{\frac{3}{2}}}$$

$$dBdt(freq) := 2 \cdot \pi \cdot freq \cdot Bcoil(distance)$$

$$Einduced\ (r, freq) = \frac{area\ (r)}{circumference\ (r)} \cdot dBdt\ (freq)$$

$$Efield\ (r, freq) = r \cdot \pi \cdot freq \cdot Bcoil\ (distance)$$

FACILITATING ACCELERATION OF ADVERTISING RATES FOR MEDICAL DEVICES

CROSS-REFERENCE TO RELATED APPLICATIONS

This application claims benefit of U.S. Provisional Application Ser. No. 62/753,513, filed on Oct. 31, 2018, and entitled "FACILITATING ACCELERATION OF ADVERTISING RATES FOR MEDICAL DEVICES." The contents of U.S. Provisional Application Ser. No. 62/753,513 are incorporated herein by reference in their entirety.

FIELD

The present disclosure is generally related to medical devices and, more particularly, to systems, apparatus, methods, and computer-readable storage media that facilitate medical device communication.

BACKGROUND

Modern healthcare facilitates the ability for patients to lead healthy and full lives. Medical devices are often utilized for such medical advances. For example, medical devices such as pacemakers, implantable cardioverter-defibrillators, neurostimulators, and drug pumps can facilitate management with a wide range of ailments, including, but not limited to, cardiac arrhythmias, diabetes, and Parkinson's disease. Patients and medical care providers can monitor the medical devices and assess a patient's current and historical physiological state to identify and/or predict impending events or conditions.

Medical devices are increasing in complexity while shrinking in size. One hurdle to achieving such small and highly functional devices is efficient power management of these medical devices. In particular, many medical devices operate from power sources that have a limited lifespan and/or are not readily replaceable. Numerous processes associated with a medical device directly impact the life of a power source of the medical device. For example, a telemetry process between a medical device and another device may unnecessarily drain power from a power source of the medical device if not properly managed.

SUMMARY

The techniques of this disclosure generally relate to systems, methods, apparatuses, computer-readable storage media, and techniques for facilitating accelerated advertising rates (e.g., accelerated BLUETOOTH® Low Energy (BLE) advertising rates) between devices, e.g., between an implantable device and an external device.

In some examples, detection circuitry of the implantable device may detect voltage induced by an electromagnetic field at an interface between tissue of a patient and the electrodes of the implantable device, and processing circuitry of the implantable medical device may change an advertising rate used by communication circuitry of the implantable device from a first advertising rate to a second advertising rate based on the detected voltage, the second advertising rate being greater than the first advertising rate. In some examples, the detection circuitry is configured to detect the voltage based on the voltage satisfying one or more criteria, and processing circuitry is configured to broadcast advertisements at the second advertising rate based on the detected voltage satisfying the one or more criteria. In one example, the one or more criteria comprise the voltage including one or more predetermined frequencies, e.g., within a range from 150 kilohertz (kHz) to 200 kHz. In one example, the one or more criteria comprise the voltage modulating between a plurality of predetermined frequencies at a predetermined rate. In another example, the one or more criteria comprise the voltage modulating between a plurality of predetermined frequencies at least a predetermined number of times.

In one aspect, an implantable device comprises a plurality of electrodes, and detection circuitry electrically coupled to the electrodes, the detection circuitry configured to detect voltage induced by an electromagnetic field at an interface between tissue of a patient and the electrodes of the implantable device. The implantable medical device further comprises communication circuitry configured for wireless communication according to a communication protocol, and processing circuitry electrically coupled to the detection circuitry and the communication circuitry. The processing circuitry is configured to broadcast, via the communication circuitry, a first set of advertisements at a first advertising rate according to the communication protocol, determine that the detection circuitry detected voltage associated with the induced electromagnetic field, and, in response to the detection of voltage associated with the induced electromagnetic field, broadcast, via the communication circuitry, a second set of advertisements at a second advertising rate according to the communication protocol, wherein the second advertising rate is greater than the first advertising rate.

In another aspect, a method comprises broadcasting, via communication circuitry of an implantable device, a first set of advertisements at a first advertising rate according to a communication protocol. The method further comprises determining that detection circuitry of the implantable device detected voltage induced by an electromagnetic field at an interface between tissue of a patient and electrodes of the implantable device and in response to the detection of voltage associated with the induced electromagnetic field, broadcasting, via the communication circuitry, a second set of advertisements at a second advertising rate according to the communication protocol. The second advertising rate is greater than the first advertising rate.

In another aspect, a system comprises an implantable device and an external device. The implantable device comprises a plurality of electrodes, detection circuitry electrically coupled to the electrodes, communication circuitry, and processing circuitry electrically coupled to the detection circuitry and the communication circuitry. The detection circuitry is configured to detect voltage induced by an electromagnetic field at an interface between tissue of a patient and the electrodes of the implantable device. The communication circuitry is configured for wireless communication according to a first communication protocol. The processing circuitry is configured to broadcast, via the communication circuitry, a first set of advertisements at a first advertising rate according to the first communication protocol. The processing circuitry is further configured to determine that the detection circuitry detected voltage induced by an electromagnetic field and in response to the detection of the voltage induced by the electromagnetic field, broadcast, via the communication circuitry, a second set of advertisements at a second advertising rate according to the first communication protocol. The second advertising rate is greater than the first advertising rate. The external device comprises second communication circuitry configured for wireless communication according to the first communication protocol and a second communication protocol and second processing circuitry electrically coupled to the second communication circuitry. The second processing circuitry is configured to transmit, via the second communication circuitry, a wakeup signal according to the second communication protocol, the wakeup signal configured to generate the electromagnetic field to induce the voltage at the interface between the tissue of a patient and the electrodes of the implantable device. The second processing circuitry is further configured to receive, via the second communication circuitry and in response to transmitting the wakeup signal, the second set of advertisements at the second advertising rate according to the first communication protocol.

By modulating advertising rate for advertisements, the lifespan of the implantable device may be extended.

The detail of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Like reference characters denote like elements throughout the description and figures.

DETAILED DESCRIPTION

Figure 1:
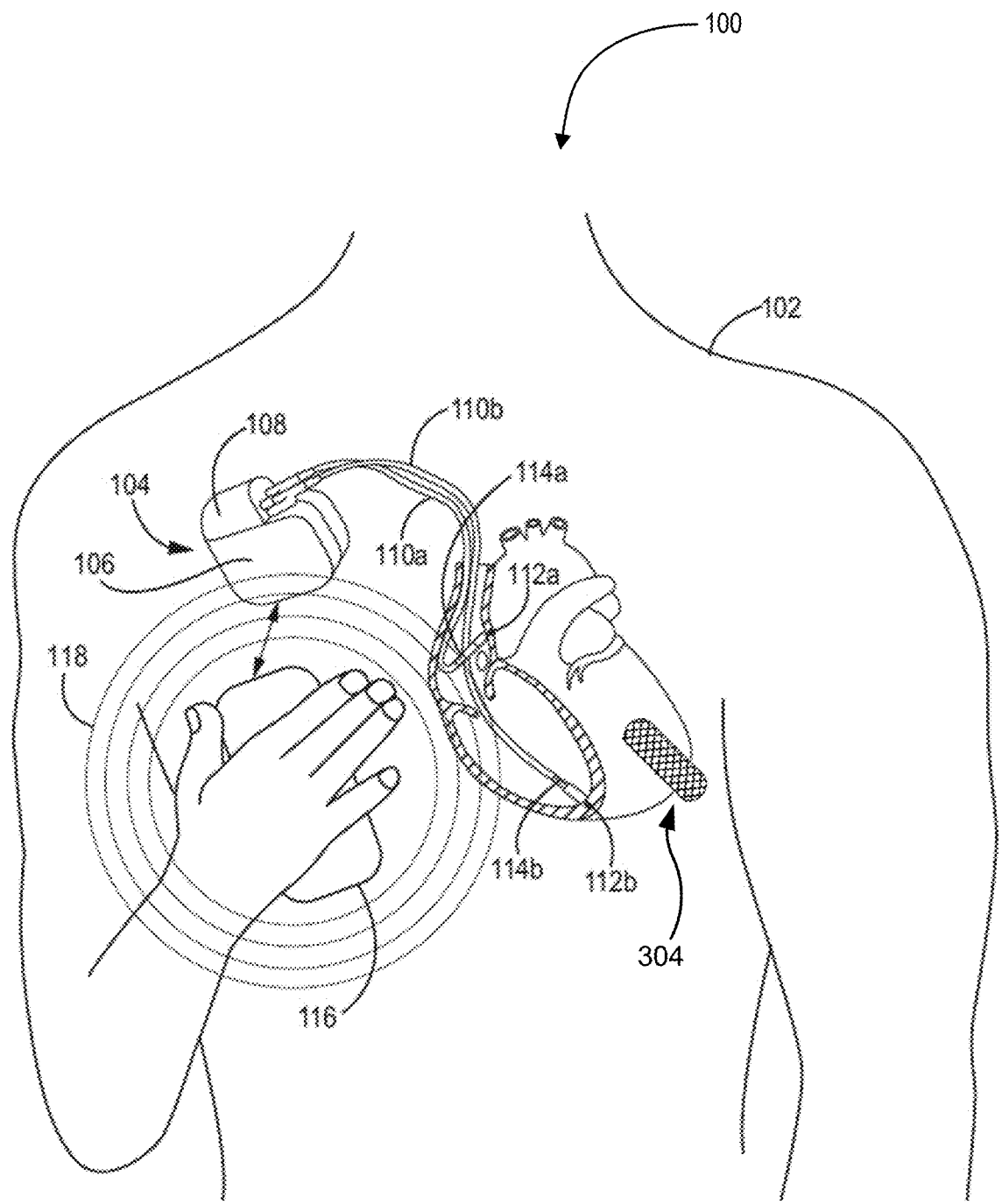
FIG. 1 illustrates the environment of an example medical device telemetry system facilitating improved telemetry between an implantable device and an external device, in accordance with one or more techniques of this disclosure.

FIG. 1 illustrates the environment of an example medical device telemetry system 100 facilitating improved telemetry between implantable and external devices, such as between one or both of implantable devices 104 and 304 and an external device 116, in accordance with one or more techniques of this disclosure. Although example system 100 includes both implantable device 104 and implantable device 304, the techniques described herein may be implemented in other systems that include only one of implantable device 104 or implantable device 304, or systems that include neither implantable device 104 nor implantable device 304.

This disclosure describes techniques for facilitating acceleration of advertising rates for medical devices, such as implantable devices 104 and 304, or other medical or non-medical devices, which may be implantable or external devices. Implantable devices 104 and 304 may be implantable medical devices (IMDs). In some examples, implantable devices 104 and 304 broadcast a first set of advertisements at a first advertising rate. The first advertising rate may be a baseline advertising rate. In some cases, the first advertising rate may be low enough that the amount of time needed for external device 116 to detect one of the advertisements and establish communication with implantable device 104 or 304 could be considered undesirable by a user of external device 116.

In some examples, e.g., assuming external device 116 does not detect one of the first set of advertisements at the first advertising rate, external device 116 may generate an electromagnetic field. Implantable device 104 or 304 may detect voltage induced by the electromagnetic field at an interface between tissue of a patient and the electrodes of the implantable device, and start broadcasting advertisements at a second advertising rate based on the detected voltage satisfying one or more criteria. The second advertising rate may be an accelerated rate that is greater than the first advertising rate. In some examples, external device 116 may generate the electromagnetic field in response to user input. In this manner, a relatively lower, first advertising rate may be used to conserve power of the implantable device for communications that are not user-requested or otherwise time sensitive.

The techniques of this disclosure are not limited to implantable devices or medical devices. The techniques may be used to modulate advertising rate for advertisements sent to establish communication between any two or more devices that can communicate with each other. A variety of devices may be configured to accelerate an advertising rate based on detecting voltage induced by an electromagnetic field at an interface between tissue of a patient and the electrodes of the device, according to the techniques described herein. Example devices that may implement the techniques described herein include wearable devices, such as watches or other external physiological sensors, wearable defibrillators, wearable pumps, or ventricular assist devices.

In some examples, implantable devices 104 and 304 are configured to detect the induced voltage based on the voltage satisfying one or more criteria. In one example, the one or more criteria comprise the voltage including one or more predetermined frequencies. In one example, the one or more criteria comprise the voltage modulating between a plurality of predetermined frequencies at a predetermined rate. In another example, the one or more criteria comprise the voltage modulating between a plurality of predetermined frequencies at least a predetermined number of times.

In some examples, implantable devices 104 and 304 record data derived from one or more sensed physiological signals of a patient, where the one or more physiological signals may be indicative of a medical condition. Implantable devices 104 and 304 may use any combination of electrodes, chemical sensors, temperature sensors, or other sensors to sense the physiological signals and store data indicative of the physiological signals in a memory. In some examples, implantable device 104 or 304 delivers therapy, such as cardiac pacing or anti-tachyarrhythmia shocks, and store data indicative of the therapy delivered. In some examples, implantable devices 104 and 304 stores data regarding the status and performance of implantable device 104 and components thereof, and operational parameters that control the functioning of implantable device 104, e.g., for sensing and/or delivering therapy.

Since implantable devices 104 and 304 are implanted within the patient, in some cases, the implantable devices may wirelessly communicate with external device 116, e.g., to transmit at least some of the data to an external device for analysis by a clinician. Additionally, a user (e.g., the patient or the clinician) may provide user input to external device 116 to control the implantable devices. External device 116 may in turn transmit instructions to implantable devices 104 and 304 based on the user input.

FIG. 1 illustrates implantable devices 104 and 304 associated with a body 102, and an external device 116. In some examples, implantable devices 104 and 304 are implanted outside of a thoracic cavity of body 102 (e.g., subcutaneously in the pectoral location illustrated in FIG. 1). In the illustrated example, implantable device 104 includes leads 110a and 110b (collectively, "leads 110") that extend to the heart of body 102. Implantable device 104 may provide cardiac monitoring, pacemaker, cardioversion, and/or defibrillation functionality. The techniques of this disclosure may be implemented with other implantable devices, such as implantable devices that do not provide therapy, implantable devices coupled to leads that extend to other locations, such as subcutaneous or substernal locations, intracardiac implantable devices, neurostimulators, or drug delivery devices. For example, implantable device 304 may be an insertable cardiac monitor (ICM) that is configured to monitor physiological parameters of a patient, but is not configured to deliver therapy to the patient. In some examples, implantable device 304 takes the form of a LINQ™ Insertable Cardiac Monitor (ICM), available from Medtronic plc, of Dublin, Ireland.

Clinicians sometimes diagnose patients with cardiac conditions based on one or more observed physiological signals collected by physiological sensors, such as electrocardiogram (ECG) electrodes, electrogram (EGM) electrodes, chemical sensors, or temperature sensors. In some cases, clinicians apply non-invasive sensors to patients in order to sense one or more physiological signals while a patent is in a clinic for a medical appointment. However, in some examples, physiological markers (e.g., irregular heartbeats) of a cardiac condition are rare. As such, in these examples, a clinician may be unable to observe the physiological markers needed to diagnose a patient with a heart condition while monitoring one or more physiological signals of the patient during a medical appointment. In the example illustrated in FIG. 1, implantable device 304 may be implanted within body 102 to continuously record one or more physiological signals of body 102 over an extended period of time.

In some examples, implantable devices 104 and 304 includes a plurality of electrodes. The plurality of electrodes are configured to detect signals that enable processing circuitry of implantable device 104 to determine current values of additional parameters associated with the cardiac and/or lung functions of body 102. In some examples, the plurality of electrodes of implantable devices 104 and 304 are configured to detect a signal indicative of an electric potential of the tissue surrounding the implantable device 104. Moreover, implantable device 104 may additionally or alternatively include one or more accelerometers, temperature sensors, chemical sensors, light sensors, pressure sensors, in some examples. Such sensors may detect one or more physiological parameters indicative of a patient condition.

External device 116 is configured to wirelessly communicate with implantable devices 104 and 304 as needed to provide or retrieve information. In some examples, external device 116 acts as an external programming device, e.g., medical device programmer, for implantable devices 104 and 304. External device 116 is an external computing device that a user, e.g., the clinician and/or the patient, may use to communicate with implantable devices 104 and 304. For example, external device 116 may be a clinician programmer that the clinician uses to communicate with implantable device 104 and update one or more settings of implantable devices 104 and 304. Additionally, or alternatively, external device 116 may be a patient programmer that allows the patient to control certain operations of implantable devices 104 and 304 and/or view and modify one or more operational parameter values of implantable devices 104 and 304. The clinician programmer may include more programming features than the patient programmer. In other words, more complex or sensitive tasks may only be allowed by the clinician programmer to prevent an untrained patient from making undesired changes to implantable device 104.

External device 116 may be a hand-held computing device with a display viewable by the user and an interface for providing input to external device 116 (i.e., a user input mechanism). For example, external device 116 may include a small display screen (e.g., a liquid crystal display (LCD) or a light emitting diode (LED) display) that presents information to the user. In addition, external device 116 may include a touch screen display, keypad, buttons, a peripheral pointing device, voice activation, or another input mechanism that allows the user to navigate through the user interface of external device 116 and provide input. If external device 116 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, external device 116 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure device. In some examples, a wireless adapter coupled to the computing device enables external device 116 to establish a secure link between the computing device and implantable devices 104 and 304.

When external device 116 is configured for use by the clinician, external device 116 may be used to transmit instructions to implantable devices 104 and 304. Example instructions may include requests to set electrode combinations for sensing and any other information that may be useful for programming into implantable devices 104 and 304. The clinician may also configure and store operational parameters for implantable devices 104 and 304 within implantable devices 104 and 304 with the aid of external device 116. In some examples, external device 116 assists the clinician in the configuration of implantable devices 104 and 304 by providing a system for identifying potentially beneficial operational parameter values.

Whether external device 116 is configured for clinician or patient use, external device 116 is configured to communicate with implantable devices 104 and 304 and, optionally, another computing device, via wireless communication. External device 116, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies).

In general, implantable devices 104 and 304 and external device 116 may exchange information using at least one communication protocol. Communication protocols define sets of rules that define one or more aspects of data exchange between two or more entities of a network. In some examples, communication protocols are stored as lists of computer-readable instructions and communication protocols may be executed by any combination of hardware (e.g., physical circuitry) and software. An organization, such as a medical device manufacturer, may create its own communication protocols, license communication protocols from a third party, use open source communication protocols, or perform any combination thereof. Example communication protocols include a Bluetooth® protocol, a BLE protocol, Medical Implant Communication Service (MICS) protocol, other proprietary or non-proprietary protocol for RF communications with medical devices, or any other communication protocols.

In some examples, implantable devices 104 and 304 broadcast advertising data packets according to a communication protocol, such as BLE, to establish a communication session with external device 116 according to the protocol. An advertising data packet generated by implantable devices 104 and 304 can be a data packet employed for advertising information to other devices (e.g., external device 116). For example, implantable devices 104 and 304 can broadcast certain data to share with other devices (e.g., external device 116) via an advertising data packet.

An advertising packet can include one or more types or sections of data that include information for other devices in close proximity to implantable device 104 that broadcasts the advertising data packet.

In some examples, an advertising data packet can facilitate a connection between implantable devices 104 and 304 and external device 116 that receives the advertising packet. In some examples, the advertising data packet can include a header portion and a data portion that can be read by other devices (e.g., external device 116) to determine whether the other devices should connect to implantable devices 104 and 304. For example, the other devices (e.g., external device 116) can establish a connection with implantable devices 104 and 304 in response to a determination that the header portion includes information relevant to the other devices (e.g., external device 116). However, the other devices (e.g., external device 116) can withhold from establishing a connection with implantable devices 104 and 304 in response to a determination that the header portion does not include information relevant to the other devices (e.g., external device 116).

Implantable devices 104 and 304 can include one or more devices, transducers and/or circuits that can convert information from one format to another format. In some examples, implantable devices 104 and 304 can include a device, a transducer and/or a circuit that can convert a signal associated with particular data for the implantable device (or, in examples in which the implantable device is an IMD, alternatively or additionally, the status of the IMD) to information for transmission by the implantable device (or generally to another signal of any number of different formats suitable for reception by external device 116). Implantable devices 104 and 304 can also include one or more power supplies. For instance, implantable devices 104 and 304 can include a battery that supplies power to the one or more devices, transducers and/or circuits.

In some examples, implantable devices 104 and 304 can insert the data associated with the implantable device (e.g., medical data, remote monitoring data, patient data, etc.) into the advertising data packet. Medical data can include medical data read or otherwise obtained by the implantable device (e.g., cardiac monitoring data, pacemaker monitoring data, glucose monitoring data, etc.), electrical signals sensed and/or generated by the implantable device, a voltage or current provided by the implantable device and/or a medical dosage provided by the implantable device. Patient data can include, for example, a name of a patient, a date of birth of a patient, a medical history associated with a patient, a medical identification or number associated with the patient or the like. Remote monitoring data can include, for example, analysis data associated with the implantable device and/or a patient, monitoring data for a condition associated with the implantable device and/or body 102 of the patient, etc. For example, implantable devices 104 and 304 can generate data associated with the implantable device. In some examples, generating the data can include can encoding the data associated with the implantable device into the advertising data packet.

Implantable devices 104 and 304 can also broadcast the advertising data packet at a defined advertising rate at a defined advertising rate during a defined interval of time. As such, in some examples, external device 116 can be provided an opportunity to receive the advertising data packet during the defined interval of time.

In an example, implantable devices 104 and 304 can broadcast an advertising data packet at a first defined advertising rate. For example, the first defined advertising rate can be a defined number of times per defined time period (e.g., once per minute, or once every two, three, or five minutes).

External device 116 can scan for the advertising data packet associated with implantable devices 104 and 304 (e.g., without connecting to the implantable devices). For example, external device 116 can include a receiver that can monitor for the advertising data packet generated by implantable devices 104 or 304. As such, if external device 116 is within a certain range from implantable devices 104 and 304 and detects the advertising data packet, external device 116 can obtain the data associated with the implantable device without connecting to the implantable device.

In some examples, external device 116 can establish a communication link with implantable device 104 or 304 based on the advertising data packet. For instance, the advertising data packet can include information indicative of a request to establish the communication link with implantable device 104 or 304. In one example, the advertising data packet can include an identifier for a particular communication channel. In another example, the advertising data packet can include an identifier for network device associated with a particular communication channel.

After establishment of the communication link between implantable device 104 or 304 and external device 116, in some examples, external device 116 and the implantable device can exchange one or more data packets. For example, after a communication link is established between external device 116 and the implantable device (e.g., based on detection by external device 116 of an advertising data packet that includes data associated with the implantable device), external device 116 can communicate with the implantable device to exchange data with the implantable device. In an example, external device 116 can read data captured by the implantable device (e.g., electrogram data, etc.) during the communication. The implantable device can also transmit sensed physiological data, diagnostic determinations made based on the sensed physiological data, implantable device performance data and/or implantable device integrity data to external device 116.

In some examples, external device 116 can include coils for inductive coupling with another device, as well as a transmitter, a receiver, or a transceiver. Such components typically leverage inductive coupling and/or propagation of electromagnetic waves to communicate with other devices in close proximity to external device 116. According to the techniques described herein, external device 116 may use these components to generate an electromagnetic field that induces a voltage at the electrodes of implantable device 104 and/or 304, e.g., in order to cause the implantable device to alter, e.g., accelerate, its advertising rate.

In one example, implantable devices 104 and 304 can be configured to be inductively coupled with external device 116 via a magnetic field 118, in response to or based on the presence of external device 116 relative to the implantable device. For example, magnetic field 118 may induce or generate a voltage at an interface between tissue of body 102 and electrodes of the implantable device. Implantable devices 104 and 304 may include circuitry configured to detect the induced voltage, and may increase its advertising rate based on detecting the induced voltage.

In some examples, external device 116 may receive a user input via a user interface, and in responsive to receiving the user input, transmit generate electromagnetic field 118. In some examples, external device 116 may generate electromagnetic field 118 as a wakeup signal to implantable device 104 and/or 304. The wakeup signal may be configured to generate electromagnetic field 118 to induce voltage at the interface between the tissue of body 102 and the electrodes of the implantable device.

The voltage induced by electromagnetic field 118 can be detected by implantable devices 104 and/or 304 and cause the implantable device to start broadcasting advertisements at a second advertising rate based on the detected voltage satisfying one or more criteria. In one example, the one or more criteria comprise the voltage including one or more predetermined frequencies (e.g., 150 kilohertz (kHz) and 200 kHz). In one example, the one or more criteria comprise the voltage modulating between a plurality of predetermined frequencies at a predetermined rate (e.g., modulating between 150 kHz and 200 kHz at a predetermined rate). In another example, the one or more criteria comprise the voltage modulating between a plurality of predetermined frequencies at least a predetermined number of times (e.g., modulating between 150 kHz and 200 kHz for 5 times). In an example, implantable devices 104 and 304 can establish a communication session with external device 116, upon detection of the voltage associated with induced electromagnetic field, based on a modulated advertising rate for an advertising data packet.

In response to the detected voltage, implantable devices 104 and 304 may change from a relatively lower advertising rate to a relatively higher advertising rate. For example, a baseline advertising rate between the implantable device and external device 116 can include advertisements occurring once every 1 to 10 minutes, whereas in response to a detected voltage, an accelerated advertising rate between the implantable device and external device 116 can be shortened to once every 1 to 10 seconds.

By modulating the advertising rate based on the detection of voltage associated with an induced electromagnetic field, performance of the power supply (e.g., the one or more power sources, the battery) included in implantable devices 104 and 304 can be improved. For instance, power consumption of implantable devices 104 and 304 may be positively correlated to advertising rate. As such, employing the dynamic advertising rate may conserve power of the power supply (e.g., the one or more power sources, the battery) of implantable devices 104 and 304. Further, in some examples, the processor and/or memory operations of the implantable devices 104, 304 and/or external device 116 can operate more efficiently due to limiting processes associated with relatively higher rate advertisement to periods in which relatively quicker establishment of a communication session is desired.

Referring to FIG. 1, in the example shown in medical device telemetry system 100, a person operating external device 116 can be a patient in which implantable devices 104 and 304 are implanted. In another example, another person (e.g., such as medical caregiver) interacting with the patient in which implantable devices 104 and 304 are implanted can operate external device 116 outside body 102 in which implantable devices 104 and 304 are located. In various examples, implantable devices 104 and 304 can include any number of different types of medical devices configured to communicate with external device 116 or another external device.

In one example, as mentioned, each of implantable devices 104 and 304 is or includes an IMD. For example, some example IMDs can include, but are not limited to, cardiac pacemakers, cardiac defibrillators, cardiac re-synchronization devices, cardiac monitoring devices, cardiac pressure monitoring devices, spinal stimulation devices, neural stimulation devices, gastric stimulation devices, diabetes pumps, drug delivery devices, and/or any other medical devices. In various examples, however, the implantable device can be or include any number of other types of implantable devices that are not IMDs.

For exemplary purposes, implantable device 104 is illustrated in medical device telemetry system 100 as an IMD implanted within the chest of a patient and configured to provide medical treatment associated with a heart disease or condition (e.g., an implantable cardioverter-defibrillator (ICD) and/or a pacemaker). In addition to the medical treatment, implantable device 104 can also be configured to provide the data packetizing and communication operations described herein. Implantable device 104 includes a housing 106 within which electrical components and one or more power sources are housed. The electrical components can be powered via the one or more power sources. A power source (not shown) can include, but is not limited to, a battery, a capacitor, a charge pump, a mechanically derived power source (e.g., microelectromechanical systems (MEMs) device), or an induction component. The various examples described herein can provide improved management of power associated with the one or more power sources.

The electrical components can vary depending on the particular features and functionality of implantable device 104. In some examples, these electrical components can include, but are not limited to, one or more processors, memories, transmitters, receivers, transceivers, sensors, sensing circuitry, therapy circuitry, antennas and other components. In an example, the electrical components can be formed on or within a substrate that is placed inside housing 106. Housing 106 can be formed from conductive materials, non-conductive materials or a combination thereof. For example, housing 106 can include a conductive material, such as metal or metal alloy, a non-conductive material such as glass, plastic, ceramic, etc., or a combination of conductive and non-conductive materials. In some examples, the housing 106 can be a biocompatible housing (e.g., a liquid crystal polymer, etc.).

In the example of FIG. 1, implantable device 104 is an IMD and further includes leads 110 connected to housing 106. Leads 110 extend into the heart and respectively include one or more electrodes. For example, as depicted in medical device telemetry system 100, leads 110a, b can include respective tip electrodes 112a, b and ring electrodes 114a, b located near a distal end of their respective leads 110a, b. When implanted, tip electrodes 112a, b and/or ring electrodes 114a, b are placed relative to or in a selected tissue, muscle, nerve or other location within body 102 of the patient. As depicted in medical device telemetry system 100, tip electrodes 112a, b are extendable helically shaped electrodes to facilitate fixation of the distal end of leads 110a, b to the target location within body 102 of the patient. In this manner, tip electrodes 112a, b are formed to define a fixation mechanism. In other examples, one or both of tip electrodes 112a, b may be formed to define fixation mechanisms of other structures. In other instances, leads 110a, b may include a fixation mechanism separate from tip electrodes 112a, b. Fixation mechanisms can be any appropriate type, including a grapple mechanism, a helical or screw mechanism, a drug-coated connection mechanism in which the drug serves to reduce infection and/or swelling of the tissue, or other attachment mechanism.

Leads 110a, b are connected at a proximal end of implantable device 104 via connector block 108. Connector block 108 may include one or more receptacles that interconnect with one or more connector terminals located on the proximal end of leads 110a, b. Leads 110a, b are ultimately electrically connected to one or more of the electrical components within housing 106. One or more conductors (not shown) extend within leads 110a, b from connector block 108 along the length of the lead to engage ring electrodes 114a, b and tip electrodes 112a, b, respectively. In this manner, one or more of tip electrodes 112a, b and ring electrodes 114a, b are electrically coupled to a respective conductor within its associated lead bodies. For example, a first electrical conductor can extend along the length of the body of lead 110a from connector block 108 and electrically couple to tip electrode 112a and a second electrical conductor can extend along the length of the body of lead 110a from connector block 108 and electrically couple to ring electrode 114a. The respective conductors may electrically couple to circuitry, such as a therapy module or a sensing module, of implantable device 104 via connections in connector block 108.

In some examples, implantable device 104 is configured to deliver therapy to the heart (or other location) via the electrical conductors to one or more of electrodes 112a, b and 114a, b. In the case of pacing therapy, for example, implantable device 104 may deliver pacing pulses via a unipolar electrode configuration, e.g., using electrodes 112a, b and a housing electrode of implantable device 104. In other instances, implantable device 104 may deliver pacing pulses via a bipolar electrode configuration, e.g., using electrodes 112a, b and ring electrodes 114a, b. Implantable device 104 may also receive sensed electrical signals on the electrical conductors from one or more of electrodes 112a, b and 114a, b. Implantable device 104 may sense the electrical signals using either a unipolar or bipolar electrode configuration.

The configuration, features and functionality of implantable device 104 are merely provided as an example. In other examples, implantable device 104 can include more or fewer leads extending from housing 106. For example, implantable device 104 can be coupled to three leads, e.g., a third lead implanted within a left ventricle of the heart of the patient. In another example, implantable device 104 can be coupled to a single lead that is implanted within the ventricle of the heart of the patient. In some examples, the lead may be an extravascular lead with the electrodes implanted subcutaneously above the ribcage/sternum or underneath or below the sternum. A variety of extravascular ICDs having subcutaneous electrodes may be employed in the disclosed implantable device, including those described in U.S. Patent Publication No. 2014/0214104 (Greenhut et al.) and U.S. Patent Publication No. 2015/0133951 (Seifert et al.), each of which is hereby incorporated herein by reference in its entirety. A variety of extravascular ICD having substernal electrodes may be employed in the disclosed implantable device, including those described in U.S. Patent Publication No. 2014/0330327 (Thompson-Nauman et al.), the disclosure of which is hereby incorporated herein by reference in its entirety. In some examples, implantable device 104 can include other leads (e.g., atrial lead and/or left ventricular lead). As such, implantable device 104 can be used for single chamber or multi-chamber cardiac rhythm management therapy. In addition to more or fewer leads, one or more of the leads may include more or fewer electrodes. In instances in which implantable device 104 is used for therapy other than pacing, (e.g., defibrillation or cardioversion), the leads can include elongated electrodes, which may, in some instances, take the form of a coil. Implantable device 104 can deliver defibrillation or cardioversion shocks to the heart via any combination of the elongated electrodes and housing electrode. As another example, implantable device 104 can include leads with a plurality of ring electrodes, (e.g., as used in some implantable neurostimulators), without a tip electrode or with one of the ring electrodes functioning as the "tip electrode."

In another example, implantable device 104 may include no leads, as in the case of an intracardiac pacemaker, such as the Micra™ transcatheter pacing system (TPS) available from Medtronic plc, or a leadless pressure sensor. In the case of an intracardiac pacemaker, the device may include a housing sized to fit wholly within the patient's heart. In one example, the housing may have a volume that is less than 1.5 cubic centimeter (cc) and, more preferably, less than 1.0 cc. However, the housing may be greater than or equal to 1.5 cc in other examples. The intracardiac pacemaker includes at least two electrodes spaced apart along the outer portion of the housing for sensing cardiac electrogram signals and/or delivering pacing pulses. Example intracardiac pacemakers are described in commonly assigned U.S. Patent Publication No. 2012/0172690 (Anderson et al.), U.S. Patent Publication No. 2012/0172941 (Kenneth), and U.S. Patent Publication No. 2014/0214104 (Greenhut et al.), each of which is incorporated herein in its entirety. In the case of a leadless pressure sensor, the device may include a housing having a fixation member and a pressure sensing component. One example of a leadless pressure sensor is described in U.S. Patent Publication No. 2012/0108922 (Schell et al.), which is incorporated herein in its entirety.

Figure 2:
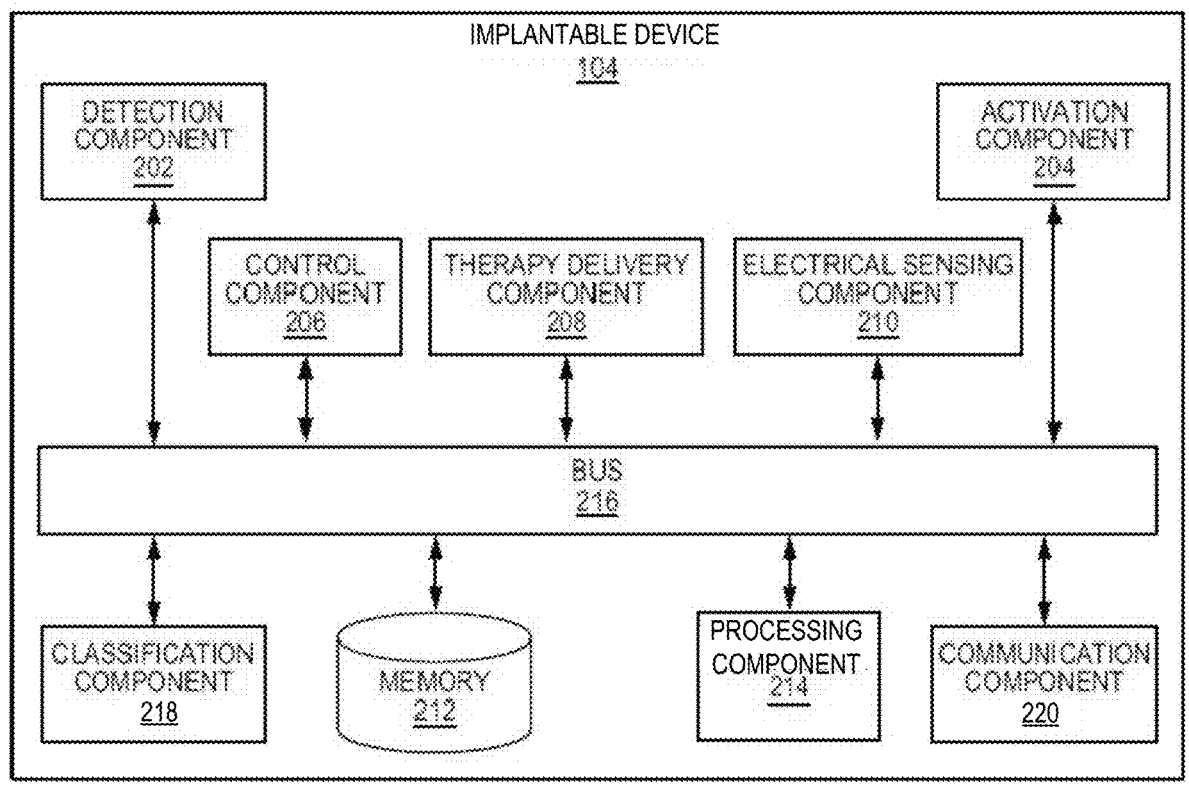
FIG. 2 is a block diagram illustrating an example configuration of components of an implantable device, in accordance with one or more techniques of this disclosure.

FIG. 2 illustrates a block diagram of an example configuration of implantable device 104 in accordance with one or more techniques of this disclosure. In the example of FIG. 2, implantable device 104 includes detection component 202, activation component 204, control component 206, therapy delivery component 208, electrical sensing component 210, memory 212, processing component 214, bus 216, classification component 218, and/or communication component 220. Although the example configuration illustrated in FIG. 2 is an example configuration of implantable device 104, implantable device 304 may include similar components and be similarly configured.

Detection component 202 may be coupled to electrodes of implantable device 104, e.g., electrodes 112, electrodes 114, and/or electrodes of housing 106. Detection component 202 can be configured to detect voltage induced by an electromagnetic field, generated by an external activator (e.g., external device 116), at an interface between tissue (e.g., tissue of body 102) and the electrodes. When external device 116 is placed over implantable device 104, the time varying magnetic field (decibels (dB)/change over time (dt)) from external device 116 induces eddy currents at the interface between the tissue and the electrodes. In some examples, external device 116 utilizes a radio frequency (RF) transmitter to generate a 150 kHz to 200 kHz electromagnetic field. Detection component 202 can be configured to detect voltage induced by the electromagnetic field based on the voltage satisfying one or more criteria, which are described herein, and avoid false detections due to noise.

In some examples, the induced electromagnetic field has three unique characteristics: a 150 kHz frequency, a 200 kHz frequency, and a modulated rate that can switch between the 150 kHz frequency and the 200 kHz frequency. For example, a noise source may have one or both of the 150 kHz frequency and 200 kHz frequency present, however, it would be unusual for that same noise source to also have the same modulation rate. Detection component 202 can avoid false detections due to noise by detecting that the voltage associated with the induced electromagnetic field satisfies one or more criteria associated with the frequency and/or modulation of the field. In some examples, in order for implantable device 104 to identify the voltage associated with the induced electromagnetic field, the generated voltage difference needs to be greater than 0.3 millivolts root mean square ($mV_{rms}$). When implantable device 104 detects voltage satisfying the one or more criteria, implantable device 104 can transition to an accelerated advertising rate (e.g., fast BLE advertising rate for a total of one minute with advertising repeated every second). The accelerated BLE advertising rate enables implantable device 104 to be configured to poll at a frequency of 1 to 2 seconds to reduce overall power consumption.

In some example, detection component 202 searches for criteria including the $f_L$ (low-frequency modulation) to $f_H$ (high-frequency modulation) transitions. The numbers of $f_L$ to $f_H$ transitions may be greater than a programmable limit. The programmable limit can be based on the circuit topology, and generally, how many counters are analyzing the frequency and how long the detection period is programmed to be. More specifically, the detection criteria search for the $f_L$ to $f_H$ transitions that are greater than the $f_L$ to carrier+$f_H$ to carrier transitions. A carrier can be a frequency band around 175 kHz. If the voltage frequency-shift keying (FSK) detection is spending a lot of time around the carrier then it does not have clean $f_L$ to $f_H$ transitions like the FSK should. Additionally, the detection criteria determine whether the frequency is not out-of-band (OOB). OOB is approximately <128.125 kHz or >221.875 kHz. The detection period can be programmable. Implantable device 104 can detect noise (e.g., OOB) via the detection component 202. If implantable device 104 detects noise, then it will not wakeup. The minimum time for this detection period is 1.7 millisecond (ms). Implantable device 104 can continually search for noise (e.g., via detection component 202) up to the detection interval end, and if the detection criteria is met then it will issue a wakeup interrupt and change the BLE advertising rate. If the detection criteria fail, it can abort early at any time between 1.7 ms and 7 ms nominal in order to save polling power. It is important to abort early if possible to save power. The detection period for a successful wakeup is approximately 7 ms nominal. The detection period is programmable, so if false wakeups become a problem, the detection period can be lengthened to improve the detection quality and avoid current drain associated with advertising if no "real" instrument (e.g., external device 116) is present. With a longer detection period, the detection quality can be improved but it can also require more current drain. However, the additional current drain may be a better tradeoff than having more false wakeups. A wakeup is an interrupt telling the device to transition from a slow advertising rate to a fast advertising rate.

Activation component 204 can be configured to initiate a BLUETOOTH® communication between implantable device 104 and external device 116. Activation component 204 initiates BLUETOOTH® communication (e.g., BLUETOOTH® Low Energy (BLE) communication protocol) between implantable device 104 and external device 116 upon detection of the voltage associated with the induced electromagnetic field that satisfies the one or more criteria (e.g., detecting the 150 kHz to 200 kHz wakeup signal). For example, implantable device 104 can be awakened and emit a signal periodically, based on the occurrence of an event or based on any number of different scenarios.

Control component 206 can communicate with therapy delivery component 208 and/or electrical sensing component 210. For example, control component 206 can communicate with therapy delivery component 208 and/or electrical sensing component 210 to facilitate sensing of cardiac electrical activity, detection of cardiac rhythms, and generation of electrical therapies based on sensed signals. Therapy delivery component 208 can be, for example, electrically coupled to tip electrodes 112a, b, ring electrodes 114a, b and/or housing 106 to deliver electrical therapies such as pacing pulses and cardioversion-defibrillation (CV/DF) shocks. In some examples, therapy delivery component 208 can be additionally coupled to tip electrodes 112a, b and/or ring electrodes 114a, b for use in delivering therapy and/or delivering mild electrical stimulation to generate a patient alert. Therapy delivery component 208 may include one or more capacitors, voltage regulators, charge pumps, current sources, and switches, as examples.

Electrical sensing component 210 can be electrically coupled to tip electrodes 112a, b and ring electrodes 114a, b carried by leads 110a, b and housing 106, which may serve as a common or ground electrode. Electrical sensing component 210 can be selectively coupled to tip electrodes 112a, b, ring electrodes 114a,b and/or housing 106 in order to, for example, monitor electrical activity of the patient's heart (e.g., electrical activity associated with tip electrodes 112a, b and/or ring electrodes 114a, b). For example, electrical sensing component 210 can include detection circuitry associated with tip electrodes 112a, b and/or ring electrodes 114a, b. In one example, electrical sensing component 210 can be enabled to monitor one or more sensing vectors selected from the tip electrodes 112a, b and/or the ring electrodes 114a, b. For example, the electrical sensing component 210 can include switching circuitry for selecting which of tip electrodes 112a, b, ring electrodes 114a, b and housing 106 are coupled to sense amplifiers or other cardiac event detectors included in electrical sensing component 210. Switching circuitry can include, for example, a switch array, a switch matrix, a multiplexer, or any other type of switching device suitable to selectively couple sense amplifiers to selected electrodes.

In some examples, electrical sensing component 210 can include multiple sensing channels for sensing multiple electrocardiogram (ECG) sensing vectors selected from tip electrodes 112a, b, ring electrodes 114a, b and/or the housing 106. For example, electrical sensing component 210 can include two sensing channels. One or more sensing channels can include a sense amplifier or other cardiac event detection circuitry for sensing cardiac events, e.g., R-waves, from the received ECG signal developed across selected electrodes (e.g., tip electrodes 112a, b and/or ring electrodes 114a, b). The cardiac event detector can operate using an auto-adjusting sensing threshold set based on a peak amplitude of a currently sensed event that can decay over time. Each time the received ECG signal crosses the auto-adjusting sensing threshold outside an absolute blanking period, a cardiac sensed event signal, such as an R-wave sensed event signal, can be produced and passed to control component 206 for use in detecting ventricular tachycardia (VT).

Control component 206 can be configured, for example, to detect VT episodes that may be life-threatening if left untreated (generally referred to herein as a "shockable rhythm") such as, for example, non-sinus VT, ventricular fibrillation, etc. The timing of R-wave sensed event signals received from electrical sensing component 210 can be used by control component 206 to determine R wave to R wave intervals between cardiac sensed event signals. Control component 206 can, for example, count RR intervals that fall into different rate detection zones for determining a ventricular rate or performing other rate-based assessments or interval-based assessments for detecting VT and discriminating VT from rhythms that do not require a CV/DF shock.

Electrical sensing component 210 can additionally or alternatively include an analog-to-digital converter that provides a digital ECG signal from one or all available sensing channels to control component 206 for further signal analysis for use in VT detection. A sensed ECG signal can be converted to a multi-bit digital signal by electrical sensing component 210 and provided to control component 206 for performing ECG morphology analysis. Analysis of the ECG signal morphology can be performed for detecting, confirming or discriminating VT.

In an example, therapy delivery component 208 can include a high voltage (HV) therapy delivery module including one or more HV output capacitors and, in some instances, a low voltage therapy delivery module. When a shockable VT rhythm is detected, the HV output capacitors can be charged to a predefined voltage level by a HV charging circuit. Control component 206 can, for example, apply a signal to trigger discharge of the HV capacitors upon detecting a feedback signal from therapy delivery component 208 that the HV capacitors have reached the voltage required to deliver a programmed shock energy. In this way, control component 206 can control operation of the high voltage output circuit of therapy delivery component 208 to deliver high energy cardioversion-defibrillation shocks using tip electrodes 112a, b, ring electrodes 114a, b and/or the housing 106.

One or more sensing channels included in electrical sensing component 210 can include spike detector circuitry for detecting non-physiological electrical signal spikes present in the cardiac electrical(s) received by electrical sensing component 210. The spike detector can produce a spike detect signal passed to control component 206 for use in detecting a lead issue as well as avoiding false detections of VT due to oversensing of electrical spikes that are not true R-waves. In some examples, electrical sensing component 210 can be configured to detect pacing pulses delivered to body 102. For example, bradycardia pacing pulses or anti-tachycardia pacing pulses delivered by implantable device 104 may be detected by the spike detector of electrical sensing component 210.

Memory 212 may be configured to store information within implantable device 104 during operation. Memory 212 may include a computer-readable storage medium or computer-readable storage device. In some examples, memory 212 includes one or more of a short-term memory or a long-term memory. Memory 212 may include, for example, random access memories (RAM), dynamic random-access memories (DRAM), static random-access memories (SRAM), magnetic discs, optical discs, flash memories, or forms of electrically programmable memories (EPROM) or electrically erasable and programmable memories (EEPROM). In some examples, memory 212 is used to store data indicative of instructions for execution by processing component 214.

In some examples, memory 212 is configured to store one or more communication protocols. Each protocol of communication protocols may define a set of rules that govern one or more aspects of data exchange between implantable device 104 and other devices (e.g., external device 116). In some examples, communication protocols are stored as lists of computer-readable instructions and communication protocols may be executed by any combination of hardware (e.g., processing circuitry in processing component 214) and software. In some examples, communication protocols include a Bluetooth® protocol such as a BLE protocol. In some examples, communication protocols exclusively include the Bluetooth® protocol. Alternatively, in other examples, communication protocols may include any combination of Bluetooth® protocols, protocols developed by the manufacturer of implantable device 104, and protocols licensed from a third-party developer.

In some examples, memory 212 is configured to store operational parameters. Operational parameters may govern aspects of the operation of implantable device 104. For example, operational parameters may include combinations of electrodes and sensors for sensing physiological signals of body 102. Additionally, or alternatively, operational parameters may include a sampling rate for sampling analog signals sensed by electrodes and sensors. Operational parameters may be updated based on instructions received from an external device (e.g., external device 116) via communication component 220.

In some examples, memory 212 is configured to store collected data. Collected data may include any data sensed, processed, or analyzed by implantable device 104, where the data is acquired via any combination of detection component 202, electrical sending component 210, and communication component 220. In some examples, collected data includes a cardiac EGM recording sensed by electrical sensing component 210 via electrodes and processed by processing component 214. Additionally, or alternatively, collected data may include data acquired by one or more chemical sensors of electrical sensing component 210, where the data is indicative of a presence of or a possibility of at least one heart condition (e.g., heart failure). Thus, in general, collected data may represent physiological signals acquired from body 102 over a period of time. In some examples, the period of time lasts for greater than 12 hours and less than 72 hours. In other examples, the period of time lasts for up to one month. Put another way, implantable device 104 is configured to continuously monitor physiological signals over the period of time and store at least some of these physiological signals in memory 212 as collected data.

Processing component 214 may include processing circuitry, which may include one or more one or more processors that are configured to implement functionality and/or process instructions for execution within implantable device 104. For example, processing circuitry may be capable of processing instructions stored in memory 212. Processing circuitry may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry may include any suitable structure, whether in hardware, software, firmware, or any combination thereof, to perform the functions ascribed herein to processing circuitry. In some examples, one or more of detection component 202, activation component 204, and control component may include processing circuitry, such as one or more microprocessors, digital signal processors (DSPs), application specific integrated circuits (ASICs), field-programmable gate arrays (FPGAs), or equivalent discrete or integrated logic circuitry, or a combination of any of the foregoing devices or circuitry.

Bus 216 may couple the various components of implantable device 104, including, but not limited to, detection component 202, activation component 204, control component 206, therapy delivery component 208, electrical sensing component 210, memory 212, processing component 214, classification component 218, and/or communication component 220.

Classification component 218 may be configured to determine a classification for data generated by implantable device 104. Data received by implantable device 104 can include, for example, medical data, remote monitoring data, patient data, status data and/or other data. The classification component 218 can also determine an urgency level for an advertising data packet generated and/or broadcasted by implantable device 104. Classification component 218 can determine an urgency level for an advertising data packet based on the classification for the data.

Communication component 220 can be configured to broadcast an advertising data packet associated with the implantable device 104. Communication component 220 can include communication circuitry, which may include any suitable hardware, firmware, software or any combination thereof for communicating with another device, such as external device 116. Under the control of processing component 214, communication circuitry may receive downlink telemetry from, as well as send uplink telemetry to external device 116. In addition, processing component 214 may communicate with a networked computing device via an external device (e.g., external device 116) and a computer network, such as the Medtronic CareLink® Network developed by Medtronic, plc, of Dublin, Ireland. Communication circuitry may include any combination of a Bluetooth® radio, an electronic oscillator, frequency modulation circuitry, frequency demodulation circuitry, amplifier circuitry, and power switches such as a metal-oxide-semiconductor field-effect transistors (MOSFET), a bipolar junction transistor (BJT), an insulated-gate bipolar transistor (IGBT), a junction field effect transistor (JFET), or another element that uses voltage for its control. In some examples, communication component 220 can broadcast an advertising data packet for implantable device 104 at a defined advertising rate based on the urgency level for the advertising data packet that is determined by classification component 218.

Figure 3:
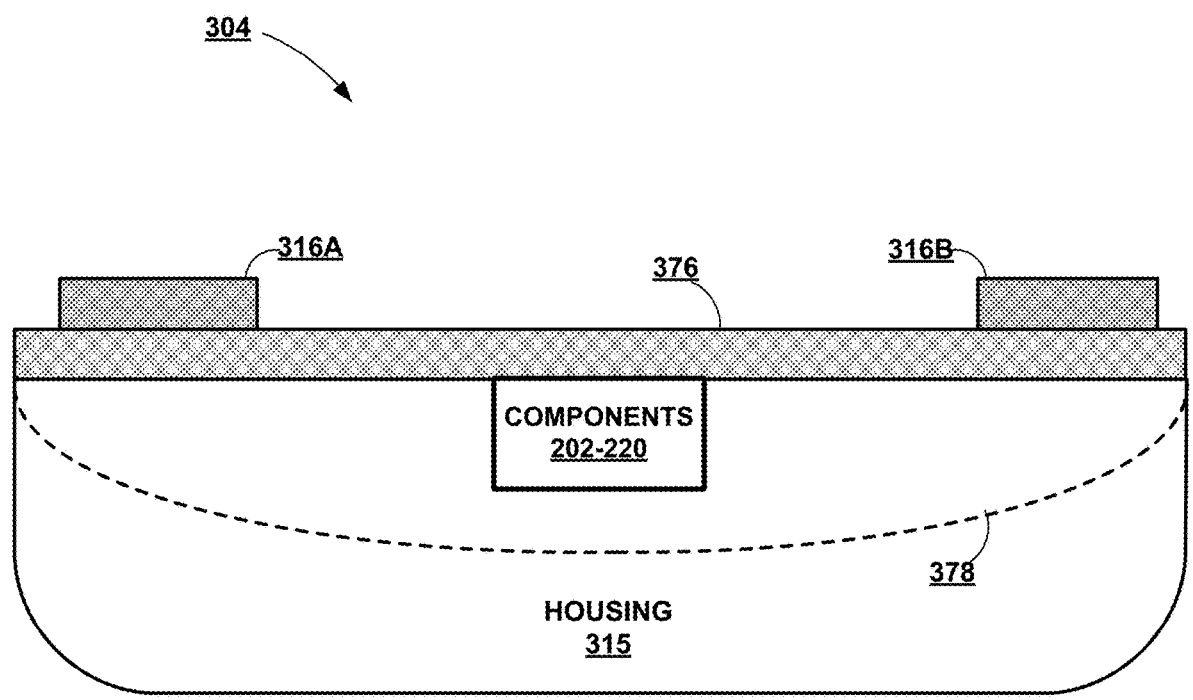
FIG. 3 is a conceptual block diagram illustrating an example configuration of components of another example implantable device, in accordance with one or more techniques of this disclosure.

FIG. 3 is a conceptual side-view diagram illustrating an example configuration of implantable device 304 that, unless otherwise indicated herein, may include the components and provide the functionality described herein with respect to implantable device 104 in FIG. 2. In the example shown in FIG. 3, implantable device 304 may include a leadless, subcutaneously implantable monitoring device having a housing 315 and an insulative cover 376. In some examples, implantable device 304 may be an insertable cardiac monitor, such as the Reveal LINQ™ Insertable Cardiac Monitoring (ICM) System available from Medtronic plc.

Electrode 316A and electrode 316B may be formed or placed on an outer surface of cover 376. Components 202-220, described above with respect to FIG. 2, may be formed or placed on an inner surface of cover 376, or otherwise within housing 315. In some examples, insulative cover 376 may be positioned over an open housing 315 such that housing 315 and cover 376 enclose components 202-220, and protect components from fluids such as body fluids.

One or more components 202-220 may be formed on the inner side of insulative cover 376, such as by using flip-chip technology. Insulative cover 376 may be flipped onto a housing 315. When flipped and placed onto housing 315, the components of implantable device 104 formed on the inner side of insulative cover 376 may be positioned in a gap 378 defined by housing 315. Electrodes 316A and 316B may be electrically connected to components 202-220 through one or more vias (not shown) formed through insulative cover 376. Insulative cover 376 may be formed of sapphire (i.e., corundum), glass, perylene, and/or any other suitable insulating material. Housing 315 may be formed from titanium or any other suitable material (e.g., a biocompatible material). Electrodes 316A and 316B may be formed from any of stainless steel, titanium, platinum, iridium, or alloys thereof. In addition, electrodes 316A and 316B may be coated with a material such as titanium nitride or fractal titanium nitride, although other suitable materials and coatings for such electrodes may be used.

Figure 4:
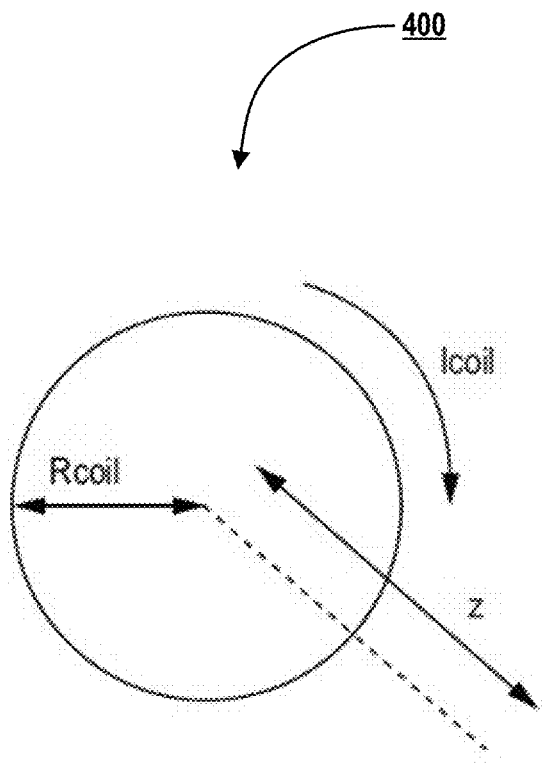
FIGS. 4 and 5 illustrate example theoretical predictions, in accordance with one or more techniques of this disclosure.
Figure 5:
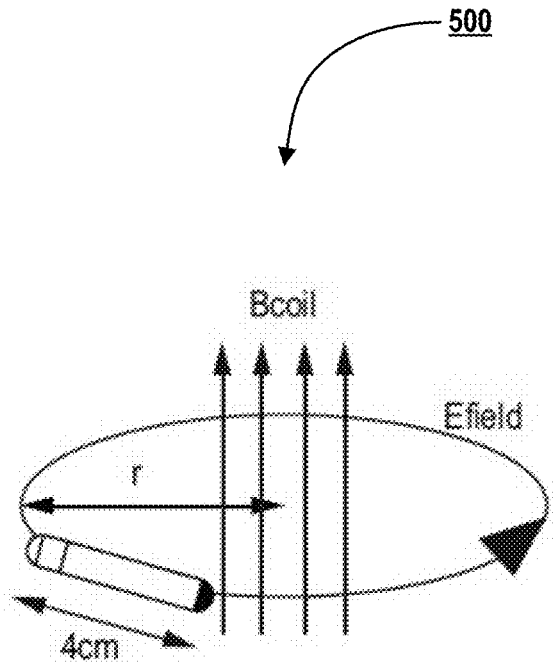

FIGS. 4 and 5 illustrate example theoretical predictions in accordance with one or more techniques of this disclosure. FIG. 4 illustrates equation $$Bcoil(z) := \frac{\mu_0}{2} \cdot Icoil \cdot \frac{Rcoil^2}{(Rcoil^2 + z^2)^{\frac{3}{2}}}$$

for the axial field strength from the wire coil and equation dBdt(freq):=2·π·freq·Bcoil(distance) is a derivative of the magnetic field (B-field). The theoretical prediction 400 depicts an alternating (AC) current through the wire coil of an external device (e.g., external device 116) that can create a magnetic field. Biot-Savart Law can be applied to determine the B-field along axis of wire coil with an electric current. The variable $\mu_0$ is the permeability constant. The Icoil is the current in a wire loop. The Rcoil is the radius of the wire coil. The z is the distance from the center of the wire coil along the axis of the coil.

FIG. 5 illustrates a derivation from the Maxwell-Faraday equation to predict the electric field strength a distance "r" from the center of a circular loop $$\left(Einduced(r, freq) := \frac{area(r)}{circumference(r)} \cdot dBdt(freq)\right)$$

with a uniform B-field. The Einduced is the induced electric field by the magnetic field at a distance "r" from the center. The area(r) is the area encompassed by a circle or radius "r". The circumference(r) is the distance around the circle, which has the same electric field strength. The dBdt(freq) is the time derivative of the alternating current (AC) magnetic field. FIG. 5 also illustrates equation Efield(r,freq):= r·π·freq·Bcoil(distance), which depicts how the induced EMF between the electrodes will be a function of the radius from the center of the geometry, the frequency, the peak magnetic field and the distance between the electrodes. The theoretical prediction 500 depicts a magnetic field (e.g., within the coils of external device 116) that can induce an electric field (E-field), which will create the voltage between the electrodes (e.g., the electrodes in implantable device 104) to cause currents to flow in the tissue (e.g., within body 102). Assuming a uniform magnetic field, the induced eddy currents (e.g., electric field, E-field) can be calculated using rearranged a magnetic flux equation. The induced eddy current creates a voltage drop (e.g., electromagnetic field (EMF)) across the two electrodes of a medical device (e.g., implantable device 104), which can be separated by 4 centimeters (cm). The voltage drop or EMF can be calculated by employing the equation emf=Efield(r,freq)·4 cm.

Figure 6:
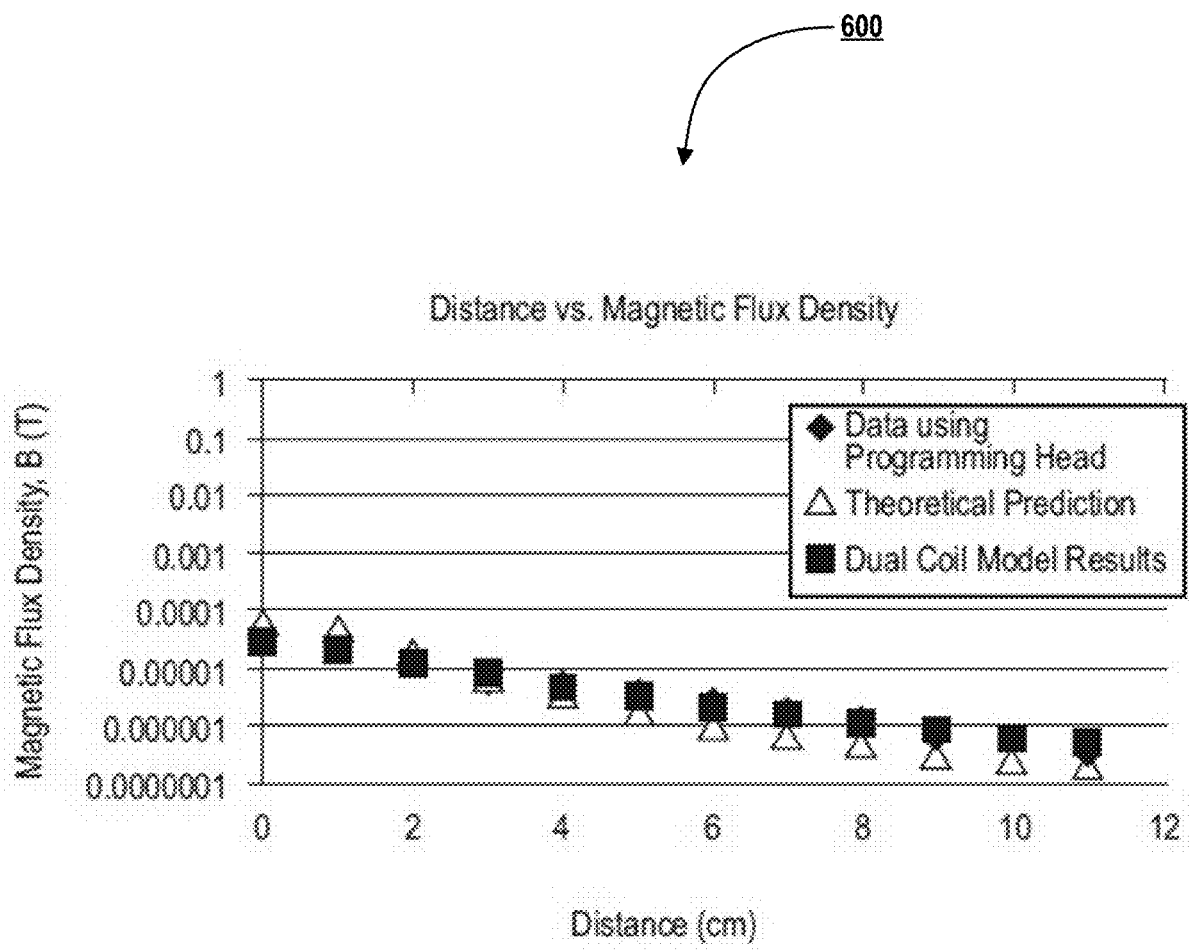
FIG. 6 illustrates an example graph depicting distance versus magnetic flux density, in accordance with one or more techniques of this disclosure.

FIG. 6 illustrates an example, non-limiting graph depicting distance versus magnetic flux density in accordance with one or more techniques of this disclosure. Graph 600 illustrates a magnetic field data from a programming head (e.g., part of external device 116) that was measured in a laboratory and compared to Maxwell three-dimensional (3D) model results. Graph 600 is a comparison of axial magnetic field data collected in a laboratory with theoretically predicted values using the above equations (e.g., from the theoretical predictions 400 and 500) and Maxwell model results. There is a strong agreement between math-based theoretical predictions, collected data, and model results, which indicates that the model results are valid for a Monte Carlo Analysis (to follow).

Figure 7:
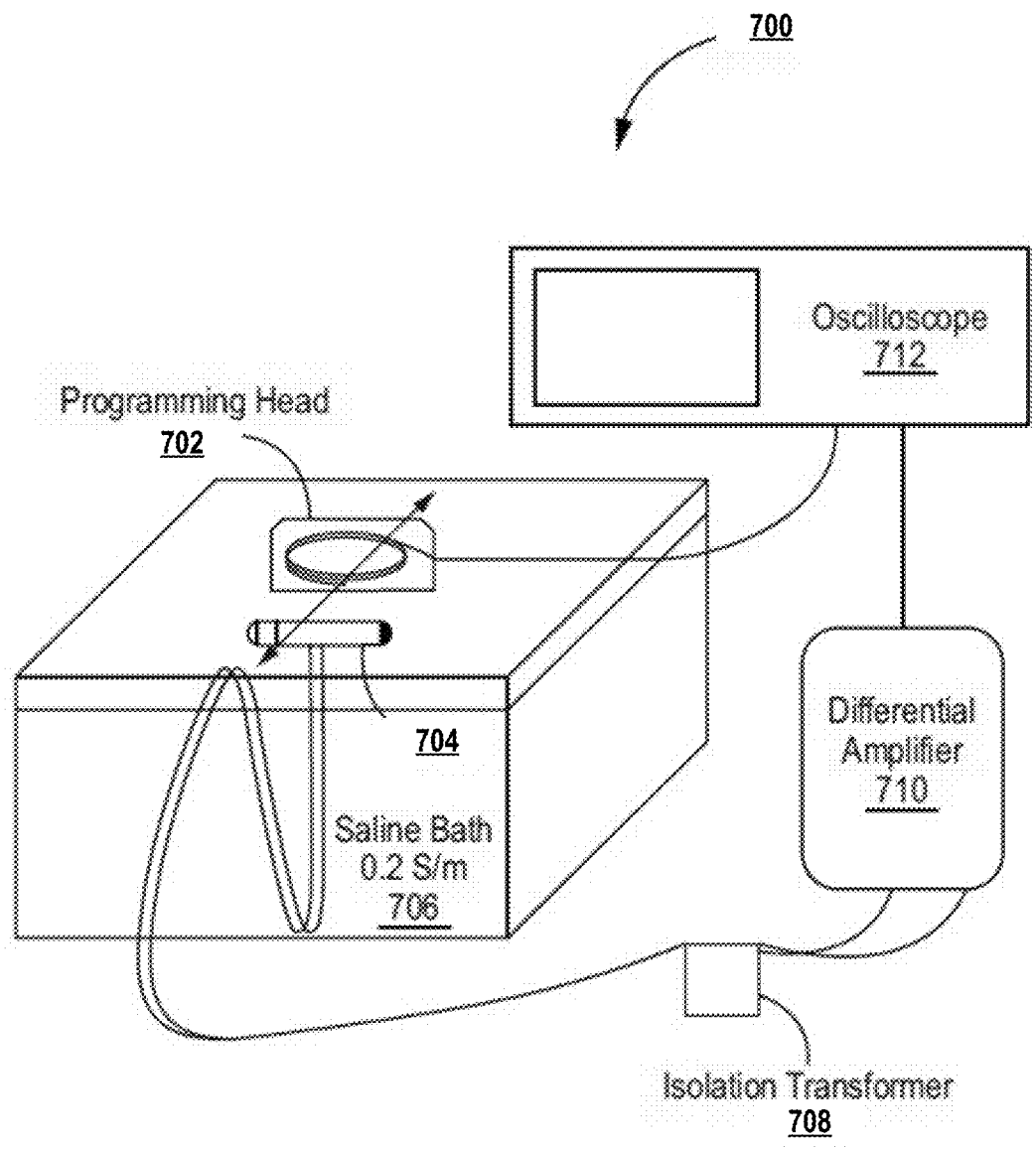
FIG. 7 illustrates an example electromagnetic field (EMF) measurement experiment, in accordance with one or more techniques of this disclosure.
Figure 8:
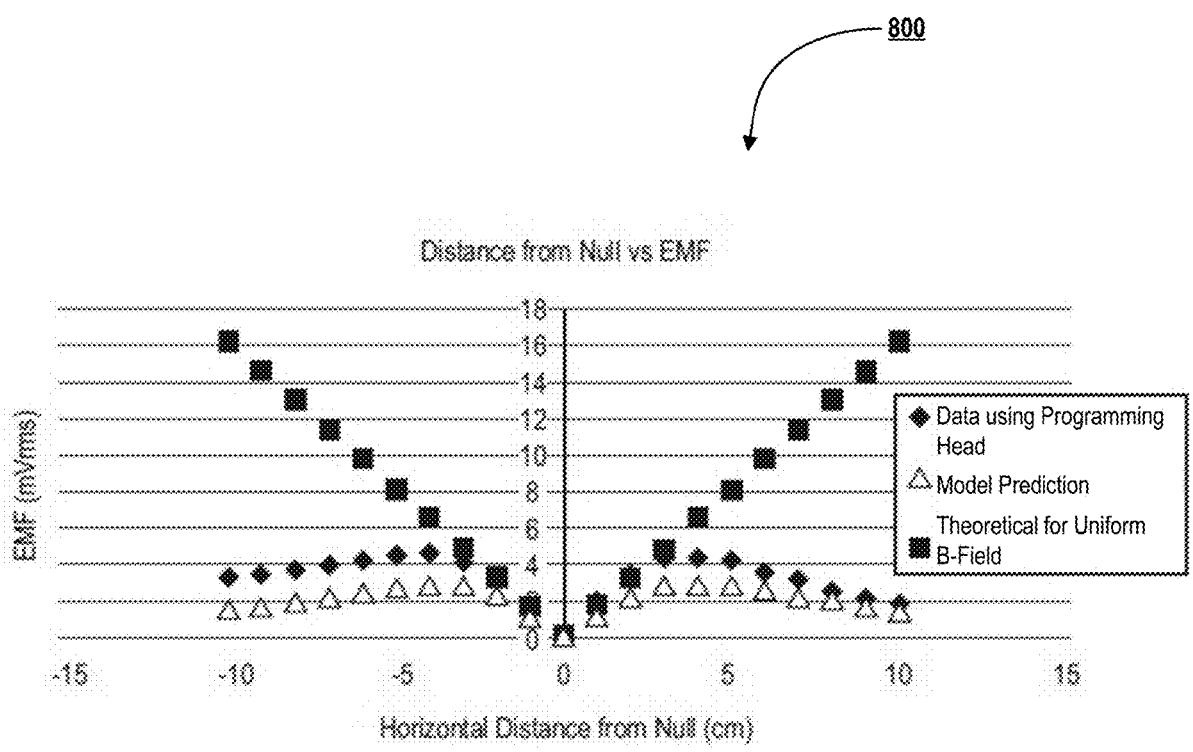
FIG. 8 illustrates an example graph depicting distance from null versus electromagnetic field, in accordance with one or more techniques of this disclosure.

With reference to FIGS. 7 and 8, an implantable device 704 (e.g., implantable device 104 or implantable device 304) was swept across a range of distances from the programmer head (e.g., part of external device 116), and the voltage across the two electrodes (e.g., of electrodes 112, 114, and housing electrode 106 of implantable device 104, or electrodes 316 of implantable device 304) was recorded.

FIG. 7 illustrates an example EMF measurement experiment in accordance with one or more techniques of this disclosure. Experiment 700 includes placing example programmer head 702 (e.g., part of an external device or external device 116) over example implantable device 704 to create an induced EMF (voltage) from the magnetic field associated with an induced electromagnetic field. The implantable device is placed in saline bath 706 that is 0.2 Siemens per meter (S/m), which is an average human body conductivity. Isolation transformer 708 couples the electrodes to a differential amplifier 710 while providing isolation to prevent the connections from affecting the measurements. Differential amplifier 710 can amplify the difference between two input voltages and output the voltage to oscilloscope 712. Oscilloscope 712 can analyze how the varying voltages change as a function of time.

FIG. 8 illustrates an example, non-limiting graph depicting distance from null versus electromagnetic field in accordance with one or more techniques of this disclosure. Graph 800 depicts a comparison of EMF data collected in a lab with theoretical predicted values (e.g., using equations from FIGS. 4 and 5) and Maxwell model results. The theoretical prediction does not account for curvature of the B-field (e.g., magnetic field) and deviates from measures for distances greater than 3 to 4 centimeters (cm).

Figure 9:
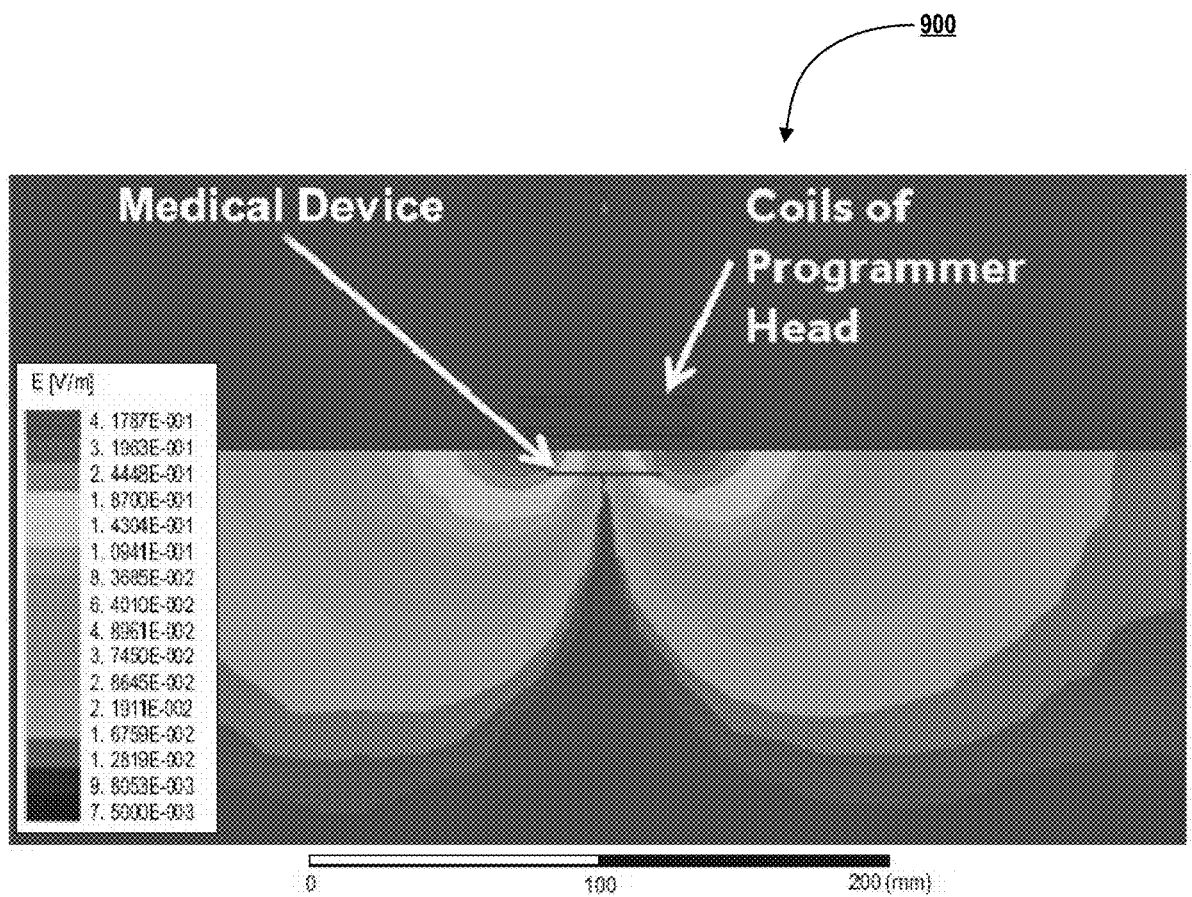
FIG. 9 illustrates an example electric field model in saline bath representing a human body, in accordance with one or more techniques of this disclosure.

FIG. 9 illustrates an example, non-limiting electric field model in saline bath representing a human body in accordance with one or more techniques of this disclosure. The model 900 depicts an E-field overlay in Maxwell 3D model created by placing the programmer head's (e.g., part of external device 116) dual coils over an implantable device (e.g., implantable device 104) placed in a saline tank representing the body. The saline tank has an average human body conductivity of 0.2 S/m similar to a human body model. The E-field created using a saline tank appears similar in shape and magnitude compared with a human body model, which validates using a saline tank for a Monte Carlo Model for faster computation.

Figure 10:
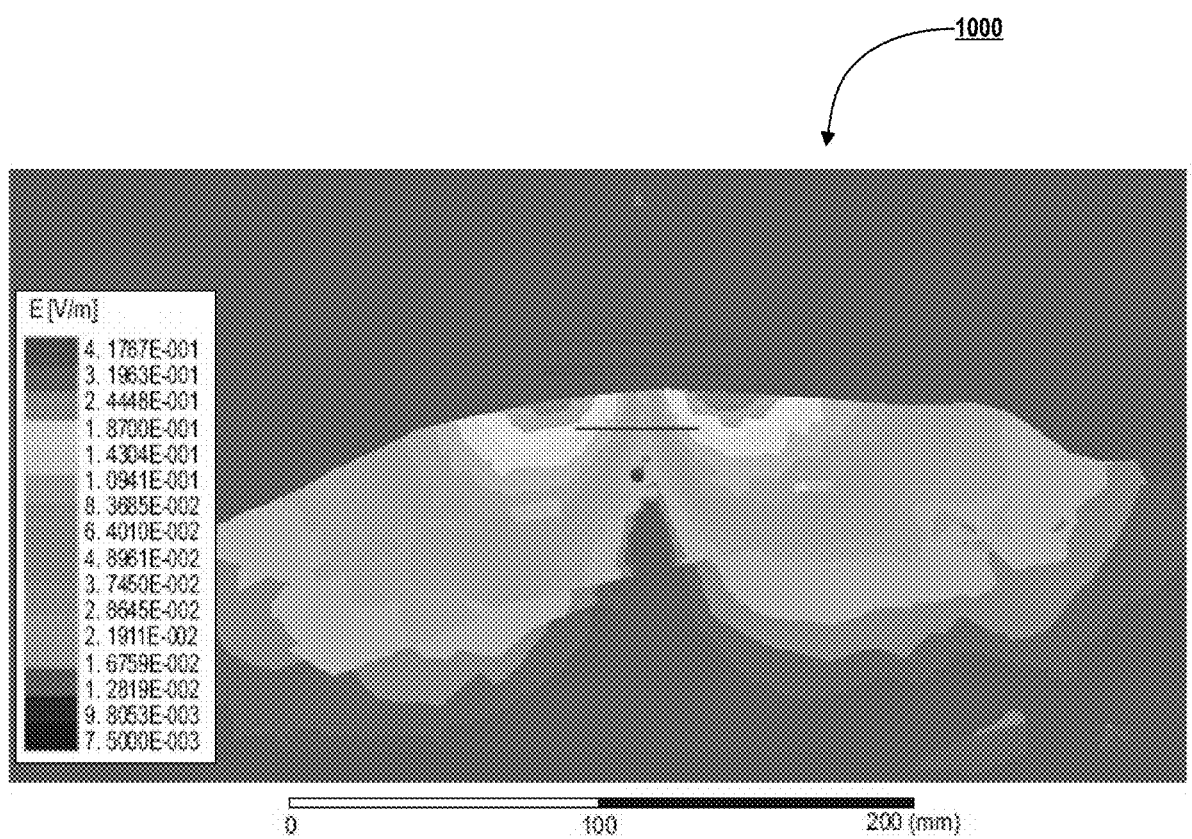
FIG. 10 illustrates an example electric field model in a human body, in accordance with one or more techniques of this disclosure.

FIG. 10 illustrates an example electric field model in a human body in accordance with one or more techniques of this disclosure. Model 1000 depicts an E-field overlay in Maxwell 3D model created by placing the programmer head's (e.g., part of external device 116) dual coils over an implantable device (e.g., implantable device 104) implanted in a human model. Further analyses were conducted to model the fat layer, which is much less conductive (0.02 S/m) than an average body conductivity (0.2 S/m). The model results as illustrated in FIG. 11 shows that this layer did not decrease EMF significantly.

Figure 11:
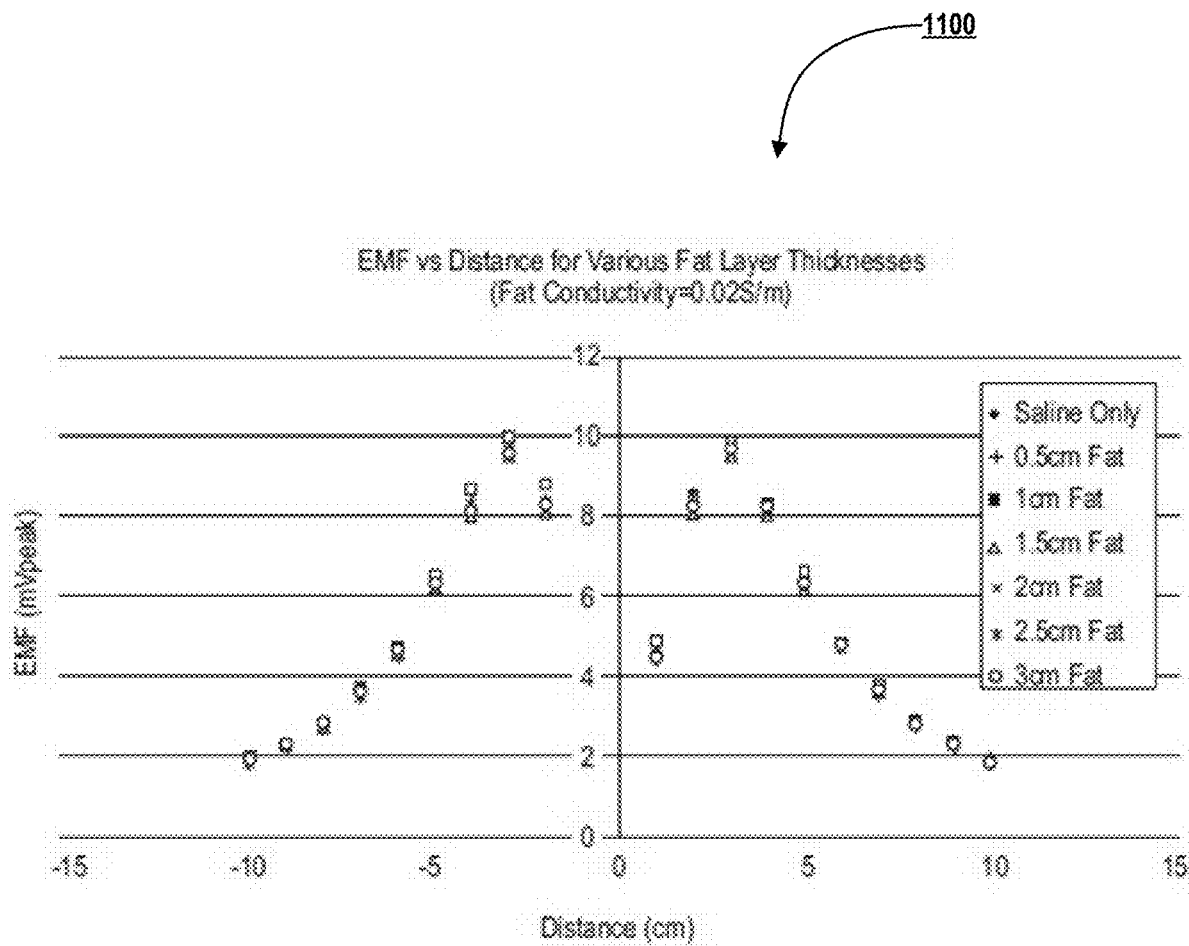
FIG. 11 illustrates an example graph depicting effects of variable fat layer on electromagnetic field, in accordance with one or more techniques of this disclosure.

FIG. 11 illustrates an example graph depicting effects of variable fat layer on the electromagnetic field in accordance with one or more techniques of this disclosure. Graph 1100 illustrates an electromagnetic field model data demonstrating the effects of variable fat layer in a saline tank model surface.

A Monte Carlo Model was designed to simulate patient variation and predict success rate. Two models were made to analyze how placement of the programmer head (e.g., part of external device 116) affected success rate. The first model is a "centered head" model in which the coils of the programmer head (e.g., part of external device 116) were positioned directly on top of the implantable device (e.g., the implantable device 104 or 304). The second model is an "offset head" approach in which the coils were placed a certain distance away from the implantable device (e.g., implantable device 104 or 304). In the first "centered head" approach, the users (e.g., doctors, clinicians, etc.) are instructed to place the programmer head (e.g., part of external device 116) directly on top of the device (e.g., implantable device 104 or 304). In the second "offset" approach, the users (e.g., doctors, clinicians, etc.) are instructed to place the programmer head (e.g., part of external device 116) offset from the implantable device (e.g., implantable device 104 or 304). The models consisted of a set of two coils representing the programmer head (e.g., part of external device 116) and a 4 cm line used to integrate the electric field between the simulated electrodes of the implantable device (e.g., implantable device 104) inside a saline tank representing the body. The programmer head coils (e.g., within external device 116) were placed at a minimum of 5 millimeters (mm) above the surface of the tank and accounted for the plastic casing of the programmer head (e.g., part of external device 116). Five parameters were considered in the Monte Carlo Model. The first parameter is the rotation of the implantable device (e.g., implantable device 104 or 304) representing variance in implantation of the implantable device. The second parameter is the implant depth of the implantable device (e.g., implantable device 104 or 304) representing variance in implantation of the implantable device. The third, fourth, and fifth parameter are X, Y, and Z-coordinate of the programmer head (e.g., part of external device 116) representing variance in placement in a clinic.

Figure 12:
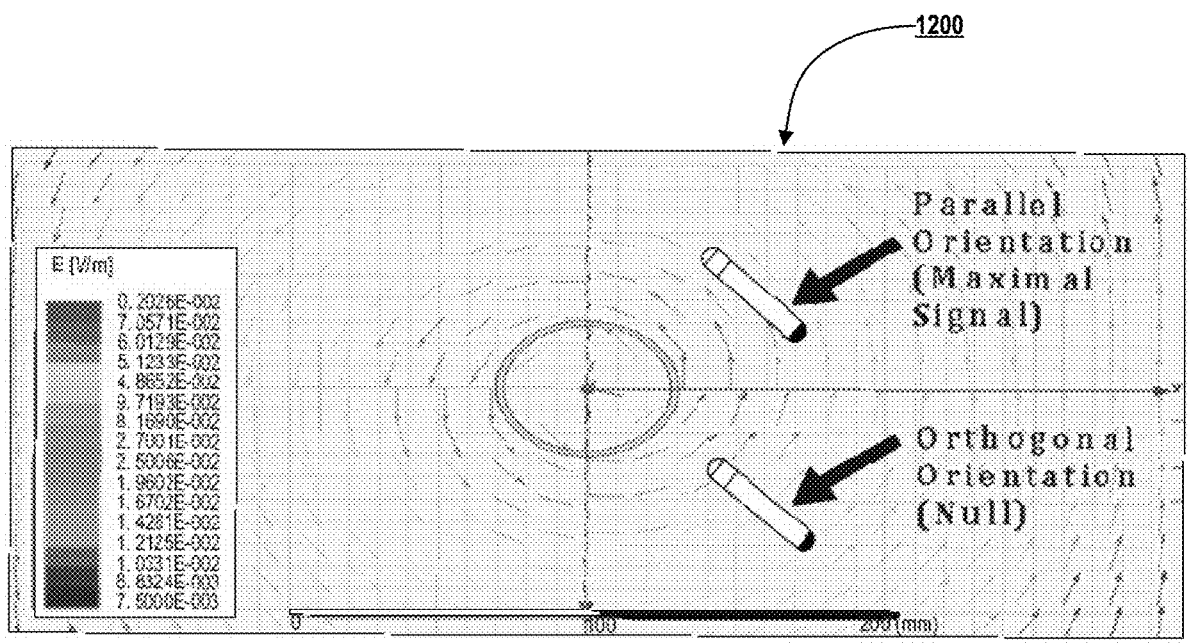
FIG. 12 illustrates an example, non-limiting electric field vector plot, in accordance with one or more techniques of this disclosure.

FIG. 12 illustrates an example electric field vector plot in accordance with one or more techniques of this disclosure. The rotation of the implantable device relative to the position of the programmer head (e.g., part of external device 116) is important because alignment with the E-field determines signal magnitude. Vector plot 1200 is an E-field vector plot showing how the orientation of a medical device (e.g., implantable device 104 or 304) corresponds to a maximum and minimum EMF signals. Maximal signal occurs when the implantable device dipole is oriented tangentially to the E-field. Nulls occur when the dipole is orthogonally oriented with the E-field.

In some examples, an implantable device (e.g., implantable device 104 or 304) can be configured to include both electrodes and induction coils to utilize both electrode based detection (e.g., first voltage associated with a first induced electromagnetic field at a first interface between tissue and electrodes of implantable device 104 or 304) and coil based detection (e.g., second voltage associated with a second induced electromagnetic field at a second interface between tissue and coils of implantable device 104 or 304) to generate the wakeup signal. An implantable device that employs both electrode-based detection and coil-based detection can improve the ability to detect signals because the coil-based detection can work when the electrode-based detection has a null. For example, an implantable device (e.g., implantable device 104 or 304) that includes a coil-based detection can gain orthogonal detection mechanism when an electrode-based detection would have a null (e.g., as described in FIG. 12). An activation component (e.g., activation component 204) can be configured to initiate a defined communication protocol from the implantable device based on detection of the first voltage or the second voltage.

Figure 13:
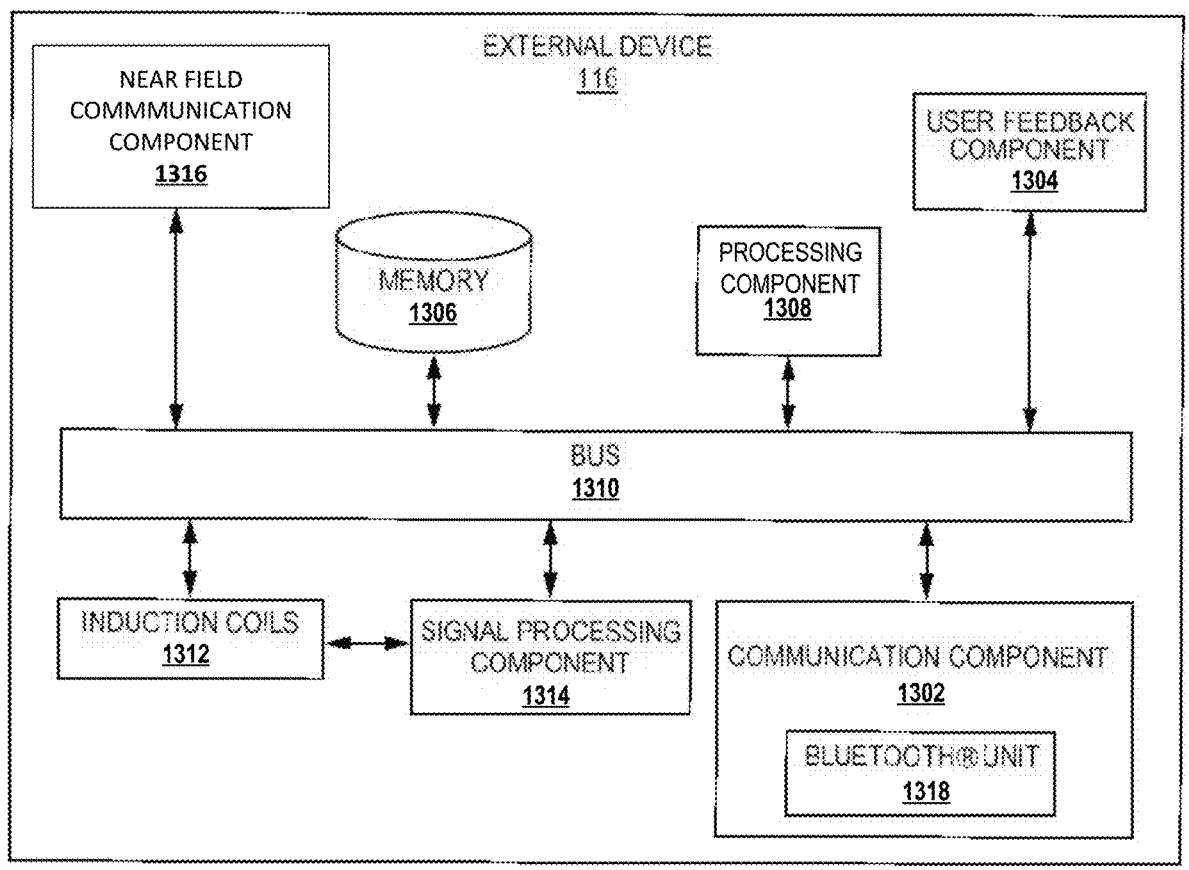
FIG. 13 illustrates a block diagram of an example external device, in accordance with one or more techniques of this disclosure.

FIG. 13 illustrates a block diagram of an example configuration of external device 116 in accordance with one or more techniques of this disclosure. External device 116 includes communication component 1302, user feedback component 1304, one or more induction coils 1312, near field communication component 1316, and BLUETOOTH® unit 1318. Aspects of the systems, apparatuses or processes explained in this disclosure can constitute one or more machine-executable components embodied within one or more machines, e.g., embodied in one or more computer-readable mediums (or media) associated with one or more machines. Such components, when executed by one or more machines, e.g., computers, computing devices, virtual machines, etc., can cause the machines to perform the operations described. External device 116 can include memory 1306 for storing computer executable components and instructions. External device 116 can further include a processing component 1308 to facilitate operation of the instructions (e.g., computer executable components and instructions) by external device 116. External device 116 can include bus 1310 that couples the various components of external device 116, including, but not limited to, communication component 1302, user feedback component 1504, memory 1306 and/or processing component 1308. In some examples, one or more of the components of external device 116, such as processing component 1308, may comprise processing circuitry, such as one or more microprocessors, digital signal processors (DSPs), application specific integrated circuits (ASICs), field-programmable gate arrays (FPGAs), or equivalent discrete or integrated logic circuitry, or a combination of any of the foregoing devices or circuitry.

External device 116 can employ telemetry communication to communicate with one or more other devices such as, for example, implantable device 104 or 304. For example, communication component 1302 of external device 116 can perform telemetry communication with other devices such as, for example, implantable device 104 or 304 using a telemetry communication protocol. In an example, communication component 1302, e.g., Bluetooth unit 1318, can scan for an advertising data packet associated with an implantable device (e.g., implantable device 104 or 304) via at least one advertising communication channel. For example, communication component 1302 can passively scan an advertising data packet associated with an implantable device (e.g., implantable device 104) without transmitting data to implantable device 104 or 304. In some examples, communication component 1302 can scan a first advertising communication channel (e.g., a 2402 MHz communication channel), a second advertising communication channel (e.g., a 2426 MHz communication channel) and/or a third advertising communication channel (e.g., a 2480 MHz communication channel) for an advertising data packet associated with an implantable device (e.g., implantable device 104 or 304). In examples in which two or more channels are scanned, the particular advertising channels can be scanned in any order.

Communication component 1302, e.g., Bluetooth® unit 1318 can also establish a communication link with implantable device 104 via a communication channel that is different than the advertising communication channel based on a determination that a criterion associated with an identified advertising data packet is satisfied. A criterion associated with an identified advertising data packet can be, for example, that the identified advertising data packet is intended for and/or can be processed by external device 116. For example, a criterion associated with an identified advertising data packet can be related to medical data associated with implantable device 104, remote monitoring data associated with implantable device 104, patient data associated with implantable device 104, status data associated with implantable device 104 and/or other data associated with implantable device 104.

User feedback component 1304 can process user input that is received by external device 116. The user input can be related implantable device 104 or 304. For instance, the user input can be related to a defined advertising rate for an advertising data packet associated with implantable device 104 or 304. Additionally or alternatively, the user input can be related to an interval of time for broadcasting an advertising data packet associated with implantable device 104 or 304. In some examples, the user input can request that external device 116 establish a communication session with implantable device 104 or 304.

In an example, user feedback component 1304 can process user input data received via external device 116. For example, user feedback component 1304 can determine a defined advertising rate and/or a defined interval of time included in the user input data. In some examples, user feedback component 1304 can analyze the user input data to determine a defined set of bits. In other examples, user feedback component 1304 can decode the user input data. The communication component 1302 can transmit the processed user input data to implantable device 104 via a first communication channel (e.g., a first BLE communication channel). Based on receiving the processed user input data, implantable device 104 or 304 (e.g., communication component 220) can broadcast an advertising data packet based on the defined advertising rate and/or a defined interval of time included in the user input data. For instance, implantable device 104 or 304 (e.g., communication component 220) can broadcast the advertising data packet (e.g., the advertising data packet that is generated based on the defined advertising rate and/or a defined interval of time included in the user input data) via a second communication channel (e.g., a second BLE communication channel). Additionally, the communication component 220 can scan for the advertising data packet (e.g., the advertising data packet that is generated based on the defined advertising rate and/or a defined interval of time included in the user input data) via the second communication channel. Based on identifying the advertising data packet via the second communication channel and/or a determination that the advertising data packet satisfies a defined criterion, communication component 220 can communicate with implantable device 104 or 304 via a third communication channel. For example, communication component 220 can communicate with implantable device 104 or 304 via a third communication channel based on a determination that the advertising data packet associated with the third communication channel includes particular data that is relevant to external device 116.

Power source consumption (e.g., battery power consumption) of external device 116 and/or implantable device 104 can be reduced by employing a modulated advertising rate for an advertising data packet associated with implantable device 104 or 304. A modulated advertising rate for an advertising data packet associated with implantable device 104 or 304 can also provide improved longevity of external device 116 and/or implantable device 104 or 304. Moreover, in some examples, compatibility with various external devices associated with a BLE protocol (e.g., off-the-shelf external devices associated with a BLE protocol) can also be improved by employing a modulated advertising rate for an advertising data packet associated with implantable device 104 or 304 and/or external device 116.

Referring to FIG. 13, external device 116 can communicate wirelessly via inductive coupling with an implantable device (e.g., implantable device 104 or 304) or other devices. To that end, as illustrated, external device 116 includes one or more induction coils 1312 functionally coupled to a signal processing component 1314. At least one of the induction coils 1312 can generate an alternating current by induction due to the presence of an alternating magnetic field generated at the implantable device, for example. The generated alternating current can be modulated according to a modulation of the alternating magnetic field. The signal processing component 1314 can receive the alternating current and can demodulate at least a portion thereof, thereby generating a signal that can convey information from the implantable device, for example. The modulation and demodulation can be implemented according to a specific protocol for communication via inductive coupling.

Signal processing component 1314 can send a signal generated in response to an inductive current to communication component 1302, which can receive and process at least a portion of the signal. Communication component 1302 also can supply information to the signal processing component 1314, which can modulate at least a portion of the information for transmission to a device inductively coupled to external device 116. To that end, in one example, signal processing component 1314 can apply an alternating current to at least one of the induction coils 1312. The alternating current can be modulated in order to generate a modulated magnetic field and, thus, send information wirelessly to such a device. Therefore, communication component 1302 can transmit, receive, and/or exchange information (such as exchanging probe messages and related response messages) with a medical device (e.g., implantable device 104) inductively coupled thereto.

External device 116 also can include near field communication component 1316 that uses induced magnetic field coupling to initiate advertising by IMD 104 or 304, which then activate, permit or otherwise facilitate wireless communication (e.g., BLUETOOTH® communication by BLUETOOTH® unit 1318) with a remote device other than a medical device. In one example, communication component 1302 can generate information to be sent to a remote device, and can send the information to BLUETOOTH® unit 1318 for modulation and encoding. BLUETOOTH® unit 1318 can send or otherwise provide the modulated and encoded information to one or more of BLUETOOTH® unit 1318, which propagate such information.

In some examples, the presence of induction coils 1312 and/or the near field communication component 1316 in external device 116 can initiate advertising by implantable device 104 or 304 using induced magnetic field coupling in order to activate, permit or otherwise facilitate BLUETOOTH® communication (e.g., concurrent or otherwise) between external device 116 and multiple implantable devices within the body. In some examples, external device 116, e.g., via communication component 1302 and/or near field communication component 1316, is configured communicate according to different communications protocols, e.g., inductive communication and RF-based communication, such as communication according to the BLE protocol. In some examples, implantable device 104 or 304 is only configured to communicate according to one of the communication protocols, e.g., the BLE protocol, but is nevertheless configured to detect voltage induced at its electrodes by an electromagnetic field generated by external device 116 according to another protocol.

Figure 14:
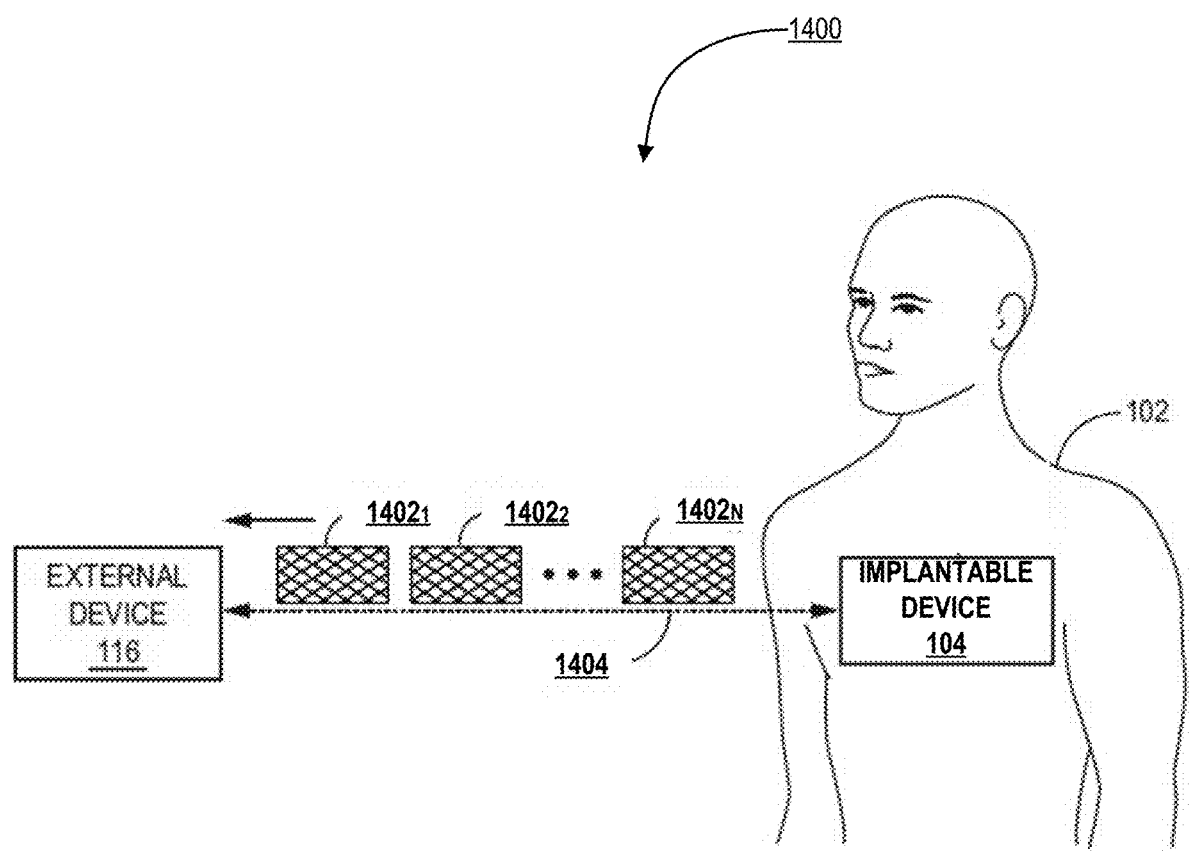
FIG. 14 illustrates an example medical device telemetry system facilitating telemetry between an implantable device and an external device, in accordance with one or more techniques of this disclosure.

FIG. 14 illustrates an example medical device telemetry system facilitating telemetry between an implantable device and an external device based on an advertising data packet in accordance with one or more techniques of this disclosure. The medical device telemetry system 1400 includes implantable device 104 and external device 116. Although implantable device 104 is illustrated in FIG. 14, the techniques described with respect to FIG. 14 may be implemented by any implantable device, such as implantable device 304.

Implantable device 104 (e.g., communication component 220) can generate an advertising data packet 1402 that includes data associated with implantable device 104. Implantable device 104 can also transmit or broadcast the advertising data packet 1402 at a defined advertising rate based on detected voltage determined by the detection component 202. In one example, implantable device 104 can repeatedly transmit advertising data packet 1402 as a first advertising data packet $1402_1$, a second advertising data packet $1402_2$, an Nth advertising data packet $1402_N$, etc., during a defined period of time (e.g., a defined interval of time). For instance, implantable device 104 can transmit the first advertising data packet $1402_1$ at a first defined time, the second advertising data packet $1402_2$ at a second defined time, the Nth advertising data packet $1402_N$ at an Nth defined time, etc. In an aspect, the defined advertising rate can be formed based on, for example, an interval of time between the first defined time and the second defined time. Advertising data packet 1402 can be communicated between implantable device 104 and external device 116 via a low power communication protocol such as, for example, BLE.

Implantable device 104 can transmit and/or broadcast the advertising data packets $1402_{1-N}$ via an advertising communication channel 1404. In one example, implantable device 104 can repeatedly transmit advertising data packet 1402 as the advertising data packets $1402_{1-N}$ via advertising communication channel 1404 during a defined period of time. A frequency of occurrence for repeatedly broadcasting advertising data packets $1402_{1-N}$ during the defined period of time can correspond to a defined advertising rate determined by classification component 218 and/or the communication component 220. For example, a rate for broadcasting advertising data packets $1402_{1-N}$ during the defined period of time can be determined based on data included in the advertising data packets $1402_{1-N}$. In another example, advertising communication channel 1404 shown in FIG. 14 can represent a set of advertising communication channels. For instance, advertising data packet 1402 can be broadcasted via advertising communication channel 1404 and one or more other advertising communication channels. In one example, the first advertising data packet $1402_1$ can be broadcasted via a first advertising communication channel associated with the advertising communication channel 1404, the second advertising data packet $1402_2$ can be broadcasted via a second advertising communication channel associated with advertising communication channel 1404, the Nth advertising data packet $1402_N$ can be broadcasted via an Nth advertising communication channel associated with the advertising communication channel 1404. In one example, advertising communication channel 1404 can be an advertising channel associated with a BLE protocol. For example, the first advertising data packet $1402_1$ can be transmitted as a first bit stream that is grouped into a set of code words, the second advertising data packet $1402_2$ can be transmitted as a second bit stream that is grouped into the set of code words, the Nth advertising data packet $1402_N$ can be transmitted as an Nth bit stream that is grouped into the set of code words, etc. In one example of system 1500, implantable device 104 can be implemented as an advertiser device and external device 116 can be implemented as a scanner device.

Figure 15:
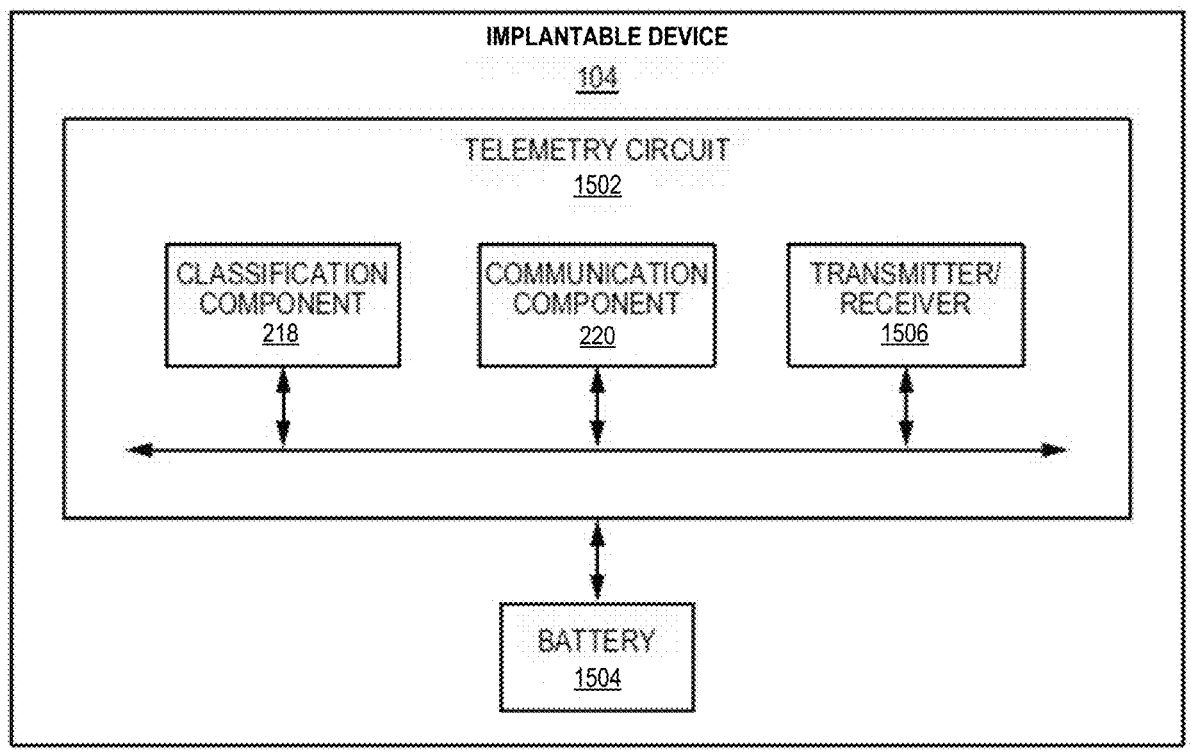
FIG. 15 is a block diagram that illustrates another example configuration of components of an implantable device, in accordance with one or more techniques of this disclosure.

FIG. 15 is a block diagram that illustrates an example configuration of implantable device 104 in accordance with one or more techniques of this disclosure. Implantable device 104 includes telemetry circuit 1502 and battery 1504. Although implantable device 104 is illustrated in FIG. 14, the techniques and features described with respect to FIG. 15 may be implemented by any implantable device, such as implantable device 304. Additionally, the features described with respect to FIG. 15 may be combined, in whole or part, with the features described with respect to FIG. 2.

Telemetry circuit 1502 can be associated with classification component 218 and/or communication component 220. For instance, in an example, telemetry circuit 1502 can include classification component 218 and/or communication component 220. Additionally, in some examples, telemetry circuit 1502 can include transmitter/receiver 1506. In one example, transmitter/receiver 1506 can be a transceiver. Battery 1504 can be, for example, a fixed battery within implantable device 104. Battery 1504 can provide power to at least telemetry circuit 1502. However, it is to be appreciated that battery 1504 can be implemented as a different type of power source for implantable device 104. For instance, in an example, battery 1504 can be a capacitor, a charge pump, a mechanically derived power source (e.g., a MEMS device), or an induction component. Therefore, by providing a modulated advertising rate for an advertising data packet as more fully disclosed herein, classification component 218 and/or communication component 220 can facilitate balancing current drain of battery 1504 to maximize utility and life of battery 1504 and/or implantable device 104. For example, classification component 218 and/or communication component 220 can be employed to calculate an advertising rate for an advertising data packet that minimally impacts battery 1504 while also broadcasting the advertising data packet and/or delivering data associated with implantable device 104 to external device 116. Longevity of battery 1504 and/or implantable device 104 can also be improved by employing a modulated advertising rate for an advertising data packet via classification component 218 and/or communication component 220, as more fully disclosed herein. Moreover, telemetry latency associated with telemetry circuit 1502 can be mitigated and/or performance of implantable device 104 can be improved by employing a modulated advertising rate for an advertising data packet via classification component 218 and/or communication component 220, as more fully disclosed herein.

In an example, communication component 220 can be configured to control operation of transmitter/receiver 1506 to facilitate establishment of a telemetry session between implantable device 104 and external device 116 and control transmission. Communication component 220 can also be configured to control operation of transmitter/receiver 1506 to facilitate reception of data packets by implantable device 104. The type of the transmitter/receiver 1506 can vary depending on the type of telemetry protocol implantable device 104 is configured to employ. In some examples, transmitter/receiver 1506 can be configured to perform different types of telemetry protocols. In other examples, implantable device 104 can include a plurality of different transmitters/receivers that are respectively configured to perform different types of telemetry communication protocols. In some examples, rather than including a transmitter and a receiver that do not share common circuitry, implantable device 104 can include a transceiver.

Figure 16:
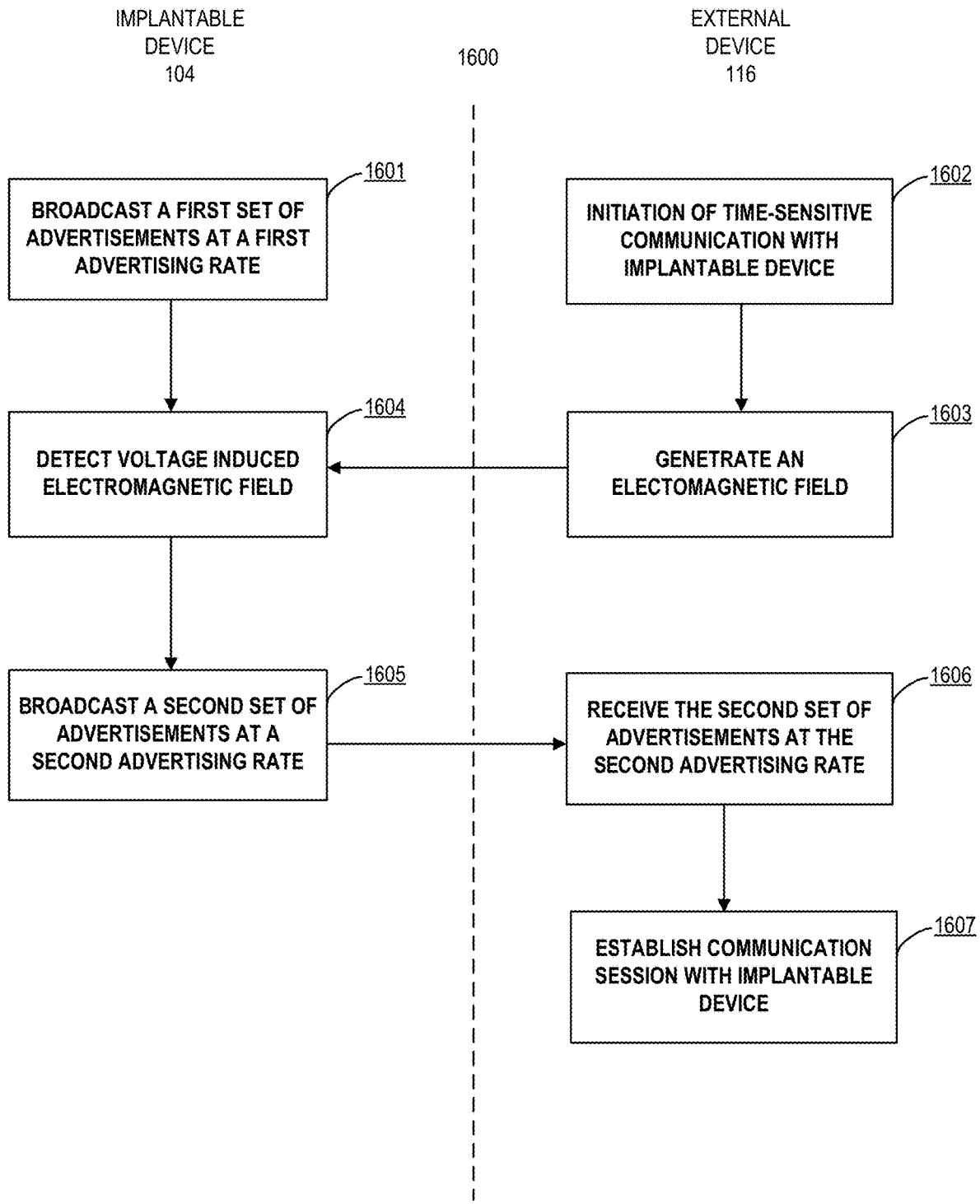
FIG. 16 illustrates a flow diagram of example method facilitating improved telemetry between an implantable device and an external device, in accordance with one or more techniques of this disclosure.

FIG. 16 is a flow diagram illustrating an example operation for facilitating acceleration of advertising rate between an implantable device and an external device. Although the example operation of FIG. 16 is described as being performed by implantable device 104 and external device 116 of FIGS. 1, 2, 13, and FIG. 15, in other examples some or all of the example operation may be performed by another devices, such as implantable device 304 of FIG. 3.

According to the example of FIG. 16, a processing circuitry of implantable device 104 may broadcast a first set of advertisements at a first advertising rate via a communication circuitry (1601), which may not be detected by external device 116 in a timely fashion for a relatively time-sensitive communication session with implantable device 104. The first advertising rate may be sufficient for opportunistic communications with a home monitor or the like, to provide routine uploads of data collected by implantable device 104 to network devices, for example. Relatively time-sensitive communications may occur during office visits or other situations in which a user of external device 116 is trying to communicate with implantable device 104.

In response to an event indicating that a relatively time-sensitive communication session with implantable device 104 should occur, such as user input requesting communication with the implantable device, external device 116 may generate an electromagnetic field in proximity to implantable device 104 to cause the implantable medical device to increase its advertising rate (1603). Implantable device 104 may detect voltage induced by the electromagnetic field (1604) at this interface of tissue with its electrodes via a detection circuitry. In response to the detected voltage, the processing circuitry of implantable device 104 may broadcast a second set of advertisements at a second advertising rate via the communication circuitry (1605), which allows external device 116 to more quickly receive the second set of advertisements (1606) and initiate the communication session with implantable device 104 (1607). The second advertising rate may be greater than the first advertising rate.

In some examples, the detection circuitry is configured to detect the voltage based on the voltage satisfying one or more criteria and processing circuitry is configured to broadcast advertisements at the second advertising rate based on the detected voltage. In one example, the one or more criteria comprise the voltage including one or more predetermined frequencies, e.g., 150 kilohertz (kHz) to 200 kHz. In one example, the one or more criteria comprise the voltage modulating between a plurality of predetermined frequencies at a predetermined rate. In another example, the one or more criteria comprise the voltage modulating between a plurality of predetermined frequencies at least a predetermined number of times.

Figure 17:
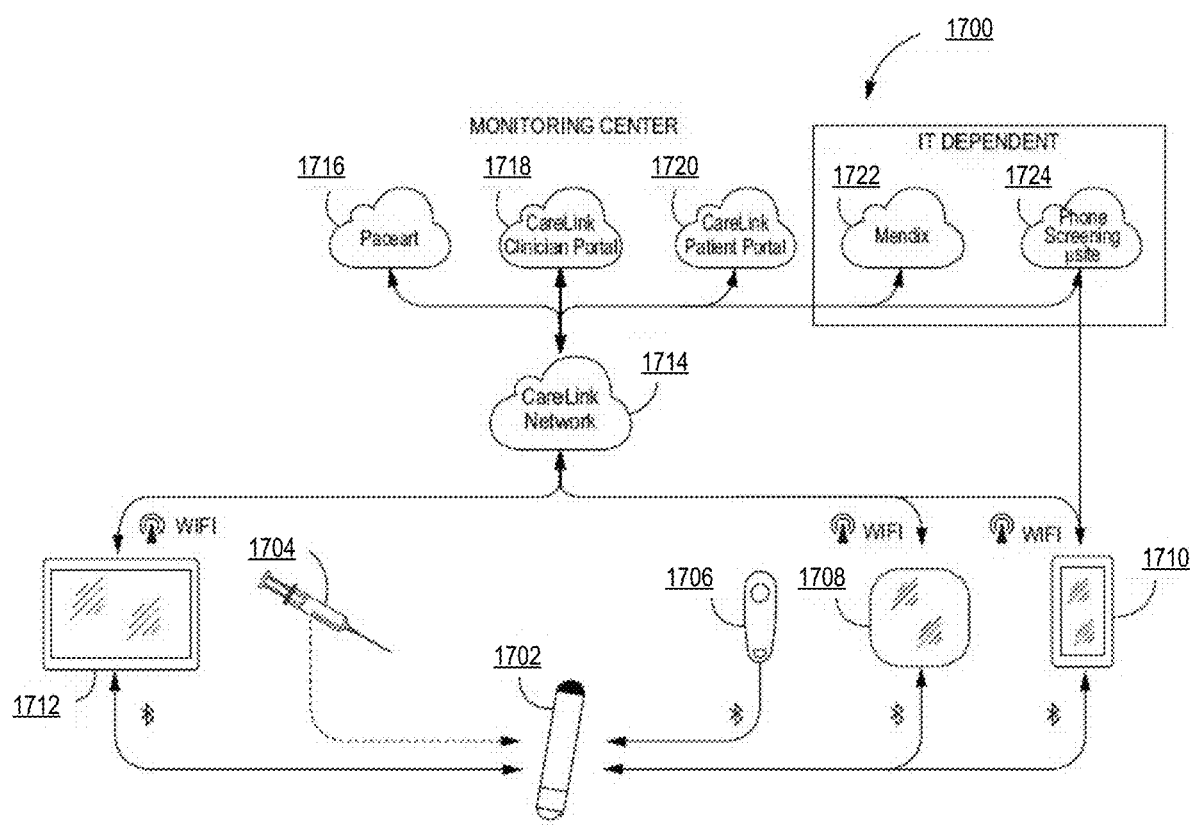
FIG. 17 illustrates a diagram of example system components, in accordance with one or more techniques of this disclosure.

FIG. 17 illustrates a diagram of an example, non-limiting system components in accordance with one or more techniques of this disclosure. The system 1700 can be configured to provide the users (e.g., doctors, clinicians, etc.) notification related to system integrity and the patient's clinical condition (e.g., fast ventricular rate) when cellular connectivity is available. The example medical device 1702 can be implanted in the body by employing insertion tool 1704. The example external device 1706 can be configured to generate a wakeup siren (e.g., detected by the detection component 202) that can initiate (e.g., via the activation component 204) a fast BLE advertising rate for 1 minute and advertising every 1 second. A user (e.g., doctors, clinicians, etc.) can receive notifications through the monitor 1708, and a patient can receive status update via the mobile app 1710 (e.g., using a mobile phone). These notifications and status update can be managed by employing the mobile manager 1712 (e.g., using a computer).

Data from example medical device 1702, example external device 1706, monitor 1708 and mobile app 1710 can be stored in the CareLink Network 1714 (e.g., a cloud network). Within the CareLink Network 1714, the data can further be separated into different portals such as Paceart 1717, CareLink Clinician Portal 1718, CareLink Patient Portal 1720, Mendix 1722 and Phone Screening μsite 1724, which can be accessed when logged in to a system that is linked to such portals. For example, the CareLink Clinician Portal 1718 can provide a user (e.g., doctor, clinician, etc.) with information necessary to arrange for a treatment plan. The CareLink Patient Portal 1720 can provide a patient with information regarding conditions that the patient has. The Paceart 1717 can provide meaningful insight into the cardiac device patient populations. The Mendix 2022 can be employed to develop web and mobile applications to help improve operational efficiency. The Phone Screening μsite 1724 can be information that is accessible through the mobile app 1710 (e.g., using a mobile phone).

Figure 18:
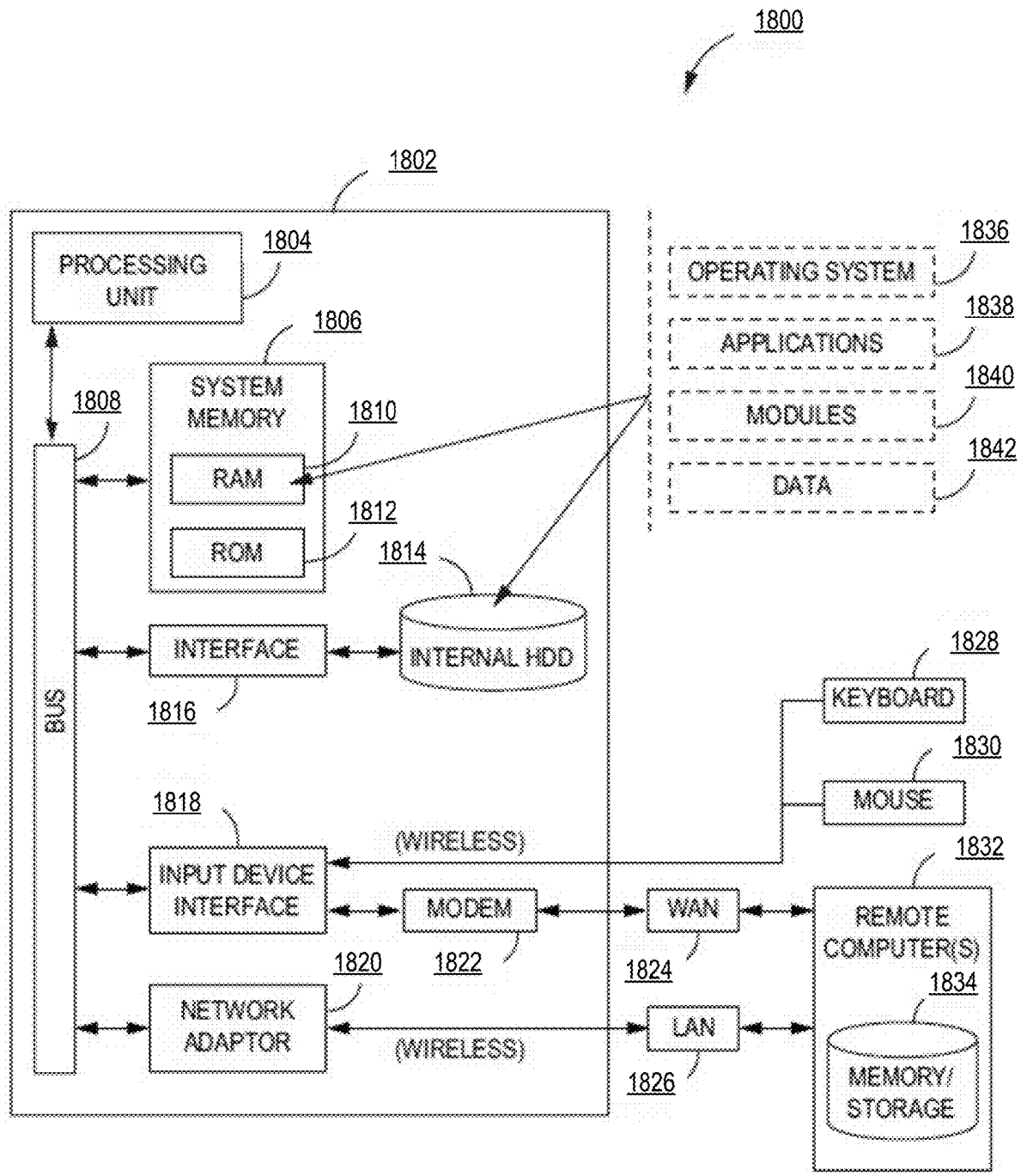
FIG. 18 illustrates a block diagram of an example computer operable to facilitate improved telemetry between an implantable device and an external device, in accordance with one or more techniques of this disclosure.

FIG. 18 illustrates a block diagram of a computer operable to facilitate improved telemetry between an implantable device and an external device in accordance with one or more techniques of this disclosure. For example, in some examples, the computer can be or be included within implantable device 104 and/or external device 116 (or any component of implantable device 104 and/or external device 116).

In order to provide additional context for one or more examples described herein, FIG. 18 and the following discussion are intended to provide a brief, general description of a suitable computing environment 1800 in which the one or more techniques of this disclosure can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, one or more of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 18, example environment 1800 for implementing one or more techniques of this disclosure includes computer 1802, computer 1802 including processing unit 1804, system memory 1806 and system bus 1808. System bus 1808 couples system components including, but not limited to, system memory 1806 to processing unit 1804. Processing unit 1804 can be any of various commercially available processors. Dual microprocessors and other multiprocessor architectures can also be employed as processing unit 1804.

System bus 1808 can be any of several types of bus structure that can further interconnect to a memory bus (with or without a memory controller), a peripheral bus, and a local bus using any of a variety of commercially available bus architectures. System memory 1806 includes RAM 1810 and ROM 1812. A basic input/output system (BIOS) can be stored in a non-volatile memory such as ROM, erasable programmable read only memory (EPROM), EEPROM, which BIOS contains the basic routines that help to transfer information between elements within computer 1802, such as during startup. RAM 1810 can also include a high-speed RAM such as static RAM for caching data.

Computer 1802 further includes internal hard disk drive (HDD) 1814 (e.g., Enhanced Integrated Drive Electronics (EIDE), Serial Advanced Technology Attachment (SATA)). HDD 1814 can be connected to system bus 1808 by hard disk drive interface 1816. The drives and their associated computer-readable storage media provide nonvolatile storage of data, data structures, computer-executable instructions, and so forth. For computer 1802, the drives and storage media accommodate the storage of any data in a suitable digital format.

A number of program modules can be stored in the drives and RAM 1810, including operating system 1836, one or more application programs 1838, other program modules 1840 and program data 1842. All or portions of the operating system, applications, modules, and/or data can also be cached in RAM 1810. The systems and methods described herein can be implemented utilizing various commercially available operating systems or combinations of operating systems.

A mobile device can enter commands and information into computer 1802 through one or more wireless input devices, e.g., wireless keyboard 1828 and a pointing device, such as wireless mouse 1830. Other input devices (not shown) can include a smart phone, tablet, laptop, wand, wearable device or the like. These and other input devices are often connected to the processing unit 1804 through input device interface 1818 that can be coupled to system bus 1808, but can be connected by other interfaces, such as a parallel port, an IEEE serial port, a game port and/or a universal serial bus (USB) port.

Computer 1802 can operate in a networked environment using logical connections via wired and/or wireless communications to one or more remote computers, such as remote computer(s) 1832. Remote computer(s) 1832 can be a workstation, a server computer, a router, a personal computer, portable computer, microprocessor-based entertainment appliance, a peer device or other common network node, and typically includes many or all of the elements described relative to computer 1802, although, for purposes of brevity, only memory/storage device 1834 is illustrated. The logical connections depicted include wired/wireless connectivity to a local area network (LAN) 1826 and/or larger networks, e.g., WAN 1824, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1802 can be connected to local network through a wired and/or wireless communication network interface or adapter 1820. Adapter 1820 can facilitate wired or wireless communication to LAN 1826, which can also include a wireless access point (AP) connected to the LAN 1826 for communicating with adapter 1820.

When used in a WAN networking environment, computer 1802 can include modem 1822 or can be connected to a communications server on WAN 1824 or has other means for establishing communications over WAN 2124, such as by way of the Internet. Modem 1822, which can be internal or external and a wired or wireless device, can be connected to system bus 1808 via input device interface 1818. In a networked environment, program modules depicted relative to computer 1802 or portions thereof, can be stored in a remote memory/storage device. It will be appreciated that the network connections shown are example and other means of establishing a communications link between the computers can be used.

Computer 1802 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 megahertz (MHz). NFC technology communication is typically over a range not exceeding 0.2 meters (m) and setup time can be less than 0.1 seconds. Low power (e.g., 15 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to one another, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The examples of devices described herein can employ artificial intelligence (AI) to facilitate automating one or more features described herein. The examples (e.g., in connection with automatically identifying acquired cell sites that provide a maximum value/benefit after addition to an existing communication network) can employ various AI-based schemes for carrying out one or more examples thereof. Moreover, the classifier can be employed to determine a ranking or priority of one or more cell sites of an acquired network. A classifier is a function that maps an input attribute vector, $x=(x1, x2, x3, x4, \ldots, xn)$, to a confidence that the input belongs to a class, that is, $f(x)=$confidence(class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the examples can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predetermined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the is intended to include, without being limited to, these and any other suitable types of memory.

In addition, in some aspects, the functionality described herein may be provided within dedicated hardware and/or software modules. Depiction of different features as modules or units is intended to highlight different functional aspects and does not necessarily imply that such modules or units may be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An implantable device, comprising:
   a plurality of electrodes;
   a power source;
   detection circuitry electrically coupled to the electrodes, the detection circuitry configured to detect voltage induced by an electromagnetic field at an interface between tissue of a patient and the electrodes of the implantable device;
   communication circuitry configured for wireless communication according to a communication protocol; and
   processing circuitry electrically coupled to the detection circuitry, the power source, and the communication circuitry, wherein the processing circuitry is configured to:
   broadcast, via the communication circuitry, a first set of advertisements at a first advertising rate according to the communication protocol;
   determine that the detection circuitry detected voltage induced by the electromagnetic field;
   determine the detected voltage satisfies one or more criteria, the one or more criteria comprising the voltage including one or more predetermined frequencies, the voltage modulating between a plurality of predetermined frequencies at a predetermined rate, or the voltage modulating between a plurality of predetermined frequencies at least a predetermined number of times; and
   in response to determining the detected voltage satisfies the one or more criteria, broadcast, powered by the power source and via the communication circuitry, a second set of advertisements at a second advertising rate according to the communication protocol, wherein the second advertising rate is greater than the first advertising rate.

2. The implantable device of claim 1, wherein the communication protocol comprises a low energy protocol.

3. The implantable device of claim 1, wherein the communication protocol comprises a first communication protocol and the electromagnetic field comprises a wakeup signal according to a second communication protocol, wherein the second communication protocol comprises a radio frequency (RF) communication protocol.

4. The implantable device of claim 1, further comprising a housing that houses the detection circuitry, the communication circuitry, and the processing circuitry, wherein the plurality of electrodes comprises housing electrodes.

5. The implantable device of claim 1, further comprising sensing circuitry configured to sense a physiological signal of the patient via the electrodes.

6. The implantable device of claim 1, wherein the detection circuitry is configured to detect the voltage based on the voltage satisfying one or more criteria and, in response to the voltage satisfying the one or more criteria, the processing circuitry is configured to transmit the second set of advertisements at the second advertising rate.

7. The implantable device of claim 1, wherein the one or more predetermined frequencies are within a range from 150 kilohertz to 200 kilohertz.

8. A method, comprising:
   broadcasting, via communication circuitry of an implantable device, a first set of advertisements at a first advertising rate according to a communication protocol;
   determining that detection circuitry of the implantable device detected voltage induced by an electromagnetic field at an interface between tissue of a patient and electrodes of the implantable device;
   determining the detected voltage satisfies one or more criteria, the one or more criteria comprising the voltage including one or more predetermined frequencies, the voltage modulating between a plurality of predetermined frequencies at a predetermined rate, or the voltage modulating between a plurality of predetermined frequencies at least a predetermined number of times; and
   in response to determining the detected voltage satisfies the one or more criteria, broadcasting, powered by a power source and via the communication circuitry, a second set of advertisements at a second advertising rate according to the communication protocol, wherein the second advertising rate is than the first advertising rate.

9. The method of claim 8, wherein the communication protocol comprises a low energy protocol.

10. The method of claim 8, wherein determining that the detection circuitry of the implantable device detected voltage induced by the electromagnetic field comprises detecting a wakeup signal according to a second communication protocol, wherein the second communication protocol comprises a radio frequency (RF) communication protocol.

11. The method of claim 8, wherein the implantable device comprises a housing that houses the detection circuitry and the communication circuitry, wherein the plurality of electrodes comprises housing electrodes.

12. The method of claim 8, further comprising sensing, via the electrodes, a physiological signal of the patient.

13. The method of claim 8, wherein the one or more predetermined frequencies are within a range from 150 kilohertz to 200 kilohertz.

14. A system, comprising:
an implantable device comprising:
- a plurality of electrodes;
- a power source;
- detection circuitry electrically coupled to the electrodes, the detection circuitry configured to detect voltage induced by an electromagnetic field at an interface between tissue of a patient and the electrodes of the implantable device;
- communication circuitry configured for wireless communication according to a first communication protocol; and
- processing circuitry electrically coupled to the detection circuitry, the power source, and the communication circuitry, wherein the processing circuitry is configured to:
  - broadcast, via the communication circuitry, a first set of advertisements at a first advertising rate according to the first communication protocol;
  - determine that the detection circuitry detected voltage induced by the electromagnetic field;
  - determine the detected voltage satisfies one or more criteria, the one or more criteria comprising the voltage including one or more predetermined frequencies, the voltage modulating between a plurality of predetermined frequencies at a predetermined rate, or the voltage modulating between a plurality of predetermined frequencies at least a predetermined number of times;
  - in response to determining the detected voltage satisfies the one or more criteria, broadcast, powered by the power source and via the communication circuitry, a second set of advertisements at a second advertising rate according to the first communication protocol, wherein the second advertising rate is greater than the first advertising rate; and
an external device comprising:
- second communication circuitry configured for wireless communication according to the first communication protocol and a second communication protocol; and
- second processing circuitry electrically coupled to the second communication circuitry, wherein the second processing circuitry is configured to:
  - transmit, via the second communication circuitry, a wakeup signal according to the second communication protocol, the wakeup signal configured to generate the electromagnetic field to induce the voltage at the interface between the tissue of a patient and the electrodes of the implantable device; and
  - receive, via the second communication circuitry and in response to transmitting the wakeup signal, the second set of advertisements at the second advertising rate according to the first communication protocol.

15. The system of claim 14, wherein the external device further comprising user interface configured to receive user input, wherein the second processing circuitry is further configured to:
- receive, via the user interface, a user input; and
- in response to receiving the user input, transmit the wakeup signal.

16. The system of claim 14, wherein the first communication protocol comprises a low energy protocol.

17. The system of claim 14, wherein the second communication protocol comprises a radio frequency (RF) communication protocol.

* * * * *